(12) United States Patent
Foerster

(10) Patent No.: US 10,499,919 B2
(45) Date of Patent: Dec. 10, 2019

(54) SYSTEMS AND METHODS FOR PERCUTANEOUS ACCESS AND FORMATION OF ARTERIOVENOUS FISTULAS

(71) Applicant: Avenu Medical, Inc., San Juan Capistrano, CA (US)

(72) Inventor: Seth Arnold Foerster, San Clemente, CA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 301 days.

(21) Appl. No.: 15/242,453

(22) Filed: Aug. 19, 2016

(65) Prior Publication Data
US 2017/0049450 A1 Feb. 23, 2017

Related U.S. Application Data

(60) Provisional application No. 62/208,353, filed on Aug. 21, 2015.

(51) Int. Cl.
*A61B 17/11* (2006.01)
*A61B 18/08* (2006.01)
(Continued)

(52) U.S. Cl.
CPC ............ *A61B 17/11* (2013.01); *A61B 18/082* (2013.01); *A61B 2017/1107* (2013.01);
(Continued)

(58) Field of Classification Search
CPC ............ A61B 17/11; A61B 2017/1107; A61B 2017/1139; A61B 18/082;
(Continued)

(56) References Cited

U.S. PATENT DOCUMENTS 5,290,278 A   3/1994  Anderson
5,329,923 A *  7/1994  Lundquist .......... A61B 18/1492
                                                        600/373
(Continued)

FOREIGN PATENT DOCUMENTS

WO     02069813 A2    9/2002
WO    2011159825 A1  12/2011
WO    2012/068273 A1  5/2012

OTHER PUBLICATIONS

International Search Report and Written Opinion dated Dec. 8, 2016, in connection with corresponding International Pat. App. No. PCT/US2016/047918.

*Primary Examiner* — Ronald Hupczey, Jr.
*Assistant Examiner* — Bradford C. Blaise
(74) *Attorney, Agent, or Firm* — Donald E. Stout; Stout, Uxa & Buyan, LLP

(57) ABSTRACT

A catheter system includes a proximal base having a distal diagonal end surface and a distal tip connected to the proximal base and movable relative to the proximal base, wherein the distal tip has a proximal diagonal end surface. The distal diagonal end surface and the proximal diagonal end surface contact opposing sides of a tissue portion to create the fistula. A peripheral edge defines the proximal distal end surface. A proximal point is disposed on the peripheral edge. The proximal point comprises a shortened angle and a fully radiused edge relative to a remaining portion of the peripheral edge and a relief recess is disposed on a distal end of the proximal base, both for the purpose of minimizing tissue snagging.

17 Claims, 19 Drawing Sheets

(51) Int. Cl.
*A61B 18/00* (2006.01)
*A61B 90/00* (2016.01)
*A61M 25/06* (2006.01)
*A61M 25/00* (2006.01)

(52) U.S. Cl.
CPC ............... *A61B 2017/1139* (2013.01); *A61B 2018/00142* (2013.01); *A61B 2018/00404* (2013.01); *A61B 2018/00577* (2013.01); *A61B 2018/00601* (2013.01); *A61B 2018/00619* (2013.01); *A61B 2018/00791* (2013.01); *A61B 2090/034* (2016.02); *A61B 2090/061* (2016.02); *A61B 2090/064* (2016.02); *A61M 25/0067* (2013.01); *A61M 25/0068* (2013.01); *A61M 25/0069* (2013.01); *A61M 25/0662* (2013.01); *A61M 25/0681* (2013.01); *A61M 2025/0687* (2013.01)

(58) Field of Classification Search
CPC ............... A61B 2018/00404; A61B 2018/00577; A61B 2018/00601; A61B 2018/00619; A61B 2090/034; A61M 25/0662; A61M 2025/0681; A61M 2025/0687; A61M 25/0067; A61M 25/0068; A61M 25/0069; A61M 25/007; A61M 25/0138; A61M 2025/006; A61M 2025/0062

See application file for complete search history.

(56) References Cited

U.S. PATENT DOCUMENTS

| | | |
|---|---|---|
| 5,425,731 A | 6/1995 | Daniel et al. |
| 5,830,222 A | 11/1998 | Makower |
| 5,830,224 A | 11/1998 | Cohn et al. |
| 6,024,739 A | 2/2000 | Ponzi |
| 6,068,637 A | 5/2000 | Popov et al. |
| 6,068,638 A | 5/2000 | Makower |
| 6,071,292 A | 6/2000 | Makower et al. |
| 6,083,223 A | 6/2000 | Baker |
| 6,099,542 A | 8/2000 | Cohn et al. |
| 6,190,353 B1 | 2/2001 | Makower et al. |
| 6,235,027 B1 | 5/2001 | Herzon |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,379,319 B1 | 4/2002 | Garibotto et al. |
| 6,398,797 B2 | 6/2002 | Bombard et al. |
| 6,409,721 B1 | 6/2002 | Wheelock et al. |
| 6,464,665 B1 | 10/2002 | Heuser |
| 6,533,778 B2 | 3/2003 | Herzon |
| 6,561,998 B1 | 5/2003 | Roth et al. |
| 6,579,311 B1 | 6/2003 | Makower |
| 6,613,081 B2 | 9/2003 | Kim et al. |
| 6,616,675 B1 | 9/2003 | Evard et al. |
| 6,699,245 B2 | 3/2004 | Dinger et al. |
| 6,699,709 B1 | 3/2004 | Bonde et al. |
| 6,709,444 B1 | 3/2004 | Makower |
| 6,726,677 B1 | 4/2004 | Flaherty et al. |
| 6,863,684 B2 | 3/2005 | Kim et al. |
| 6,908,463 B2 | 6/2005 | Treat et al. |
| 6,929,009 B2 | 8/2005 | Makower et al. |
| 7,056,325 B1 | 6/2006 | Makower et al. |
| 7,074,220 B2 | 7/2006 | Hill et al. |
| 7,159,592 B1 | 1/2007 | Makower et al. |
| 7,191,015 B2 | 3/2007 | Lamson et al. |
| 7,316,655 B2 | 1/2008 | Garibotto et al. |
| 7,351,247 B2 | 4/2008 | Kupiecki et al. |
| 7,387,636 B2 | 6/2008 | Cohn et al. |
| 7,588,566 B2 | 9/2009 | Treat et al. |
| 7,729,738 B2 | 6/2010 | Flaherty et al. |
| 7,846,172 B2 | 12/2010 | Makower |
| 7,988,690 B2 | 8/2011 | Chanduszko et al. |
| 8,236,014 B2 | 8/2012 | Brenneman et al. |
| 8,721,639 B2 | 5/2014 | Mirizzi et al. |
| 8,834,518 B2 | 9/2014 | Faller et al. |
| 2003/0040764 A1 | 2/2003 | Adams |
| 2003/0225426 A1 | 7/2003 | Treat |
| 2003/0229344 A1 | 12/2003 | Dycus |
| 2004/0073238 A1 | 4/2004 | Makower |
| 2004/0204725 A1 | 10/2004 | Bayer |
| 2005/0033330 A1 | 2/2005 | Vargas et al. |
| 2005/0038457 A1 | 2/2005 | Vargas et al. |
| 2005/0251167 A1 | 11/2005 | Voegele |
| 2006/0020265 A1 | 1/2006 | Ryan |
| 2006/0111704 A1 | 5/2006 | Brenneman et al. |
| 2006/0142788 A1 | 6/2006 | Wilson et al. |
| 2006/0189979 A1 | 8/2006 | Esch et al. |
| 2006/0217706 A1 | 9/2006 | Lau |
| 2007/0112348 A1 | 5/2007 | Eggers et al. |
| 2007/0175963 A1 | 8/2007 | Bilotti |
| 2007/0276363 A1 | 11/2007 | Patton |
| 2008/0187989 A1 | 8/2008 | McGreevy |
| 2008/0312651 A1 | 12/2008 | Pope et al. |
| 2009/0048589 A1 | 2/2009 | Takashino |
| 2009/0312783 A1 | 12/2009 | Whayne |
| 2010/0152723 A1 | 6/2010 | Esch et al. |
| 2010/0204698 A1 | 8/2010 | Chapman et al. |
| 2011/0011916 A1 | 1/2011 | Levine |
| 2011/0095067 A1 | 4/2011 | Ohdaira |
| 2011/0251608 A1 | 10/2011 | Timm et al. |
| 2011/0251609 A1 | 10/2011 | Johnson et al. |
| 2011/0306959 A1 | 12/2011 | Kellerman et al. |
| 2011/0306993 A1 | 12/2011 | Hull et al. |
| 2012/0078246 A1 | 3/2012 | Mirizzi et al. |
| 2012/0302935 A1 | 11/2012 | Miller et al. |
| 2012/0316550 A1 | 12/2012 | Lau et al. |
| 2013/0123827 A1 | 5/2013 | Kellerman et al. |
| 2013/0281998 A1 | 10/2013 | Kellerman et al. |
| 2014/0039478 A1 | 2/2014 | Hull et al. |
| 2014/0094791 A1 | 4/2014 | Hull et al. |
| 2014/0142561 A1 | 5/2014 | Reu et al. |

\* cited by examiner

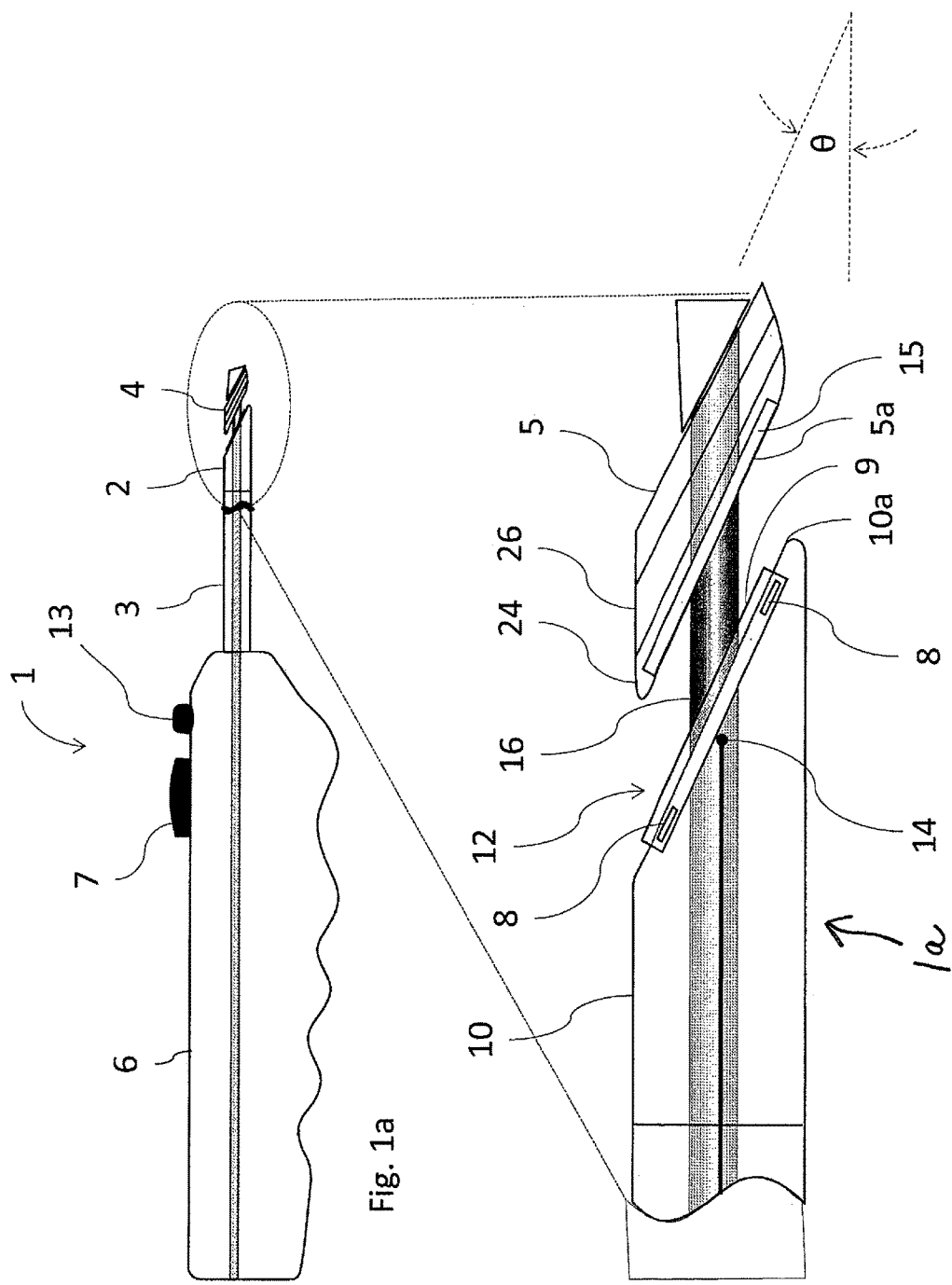

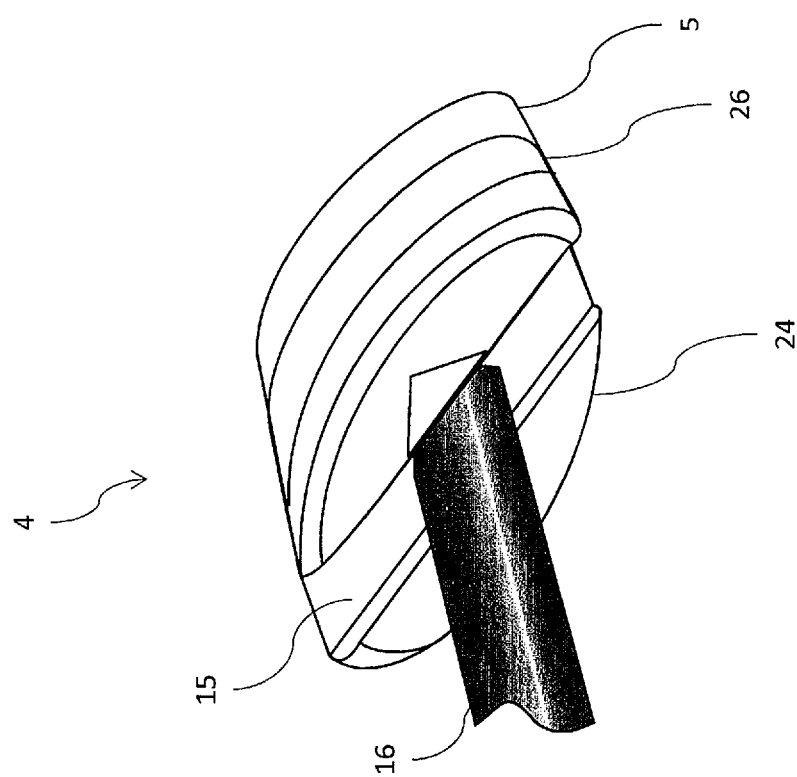

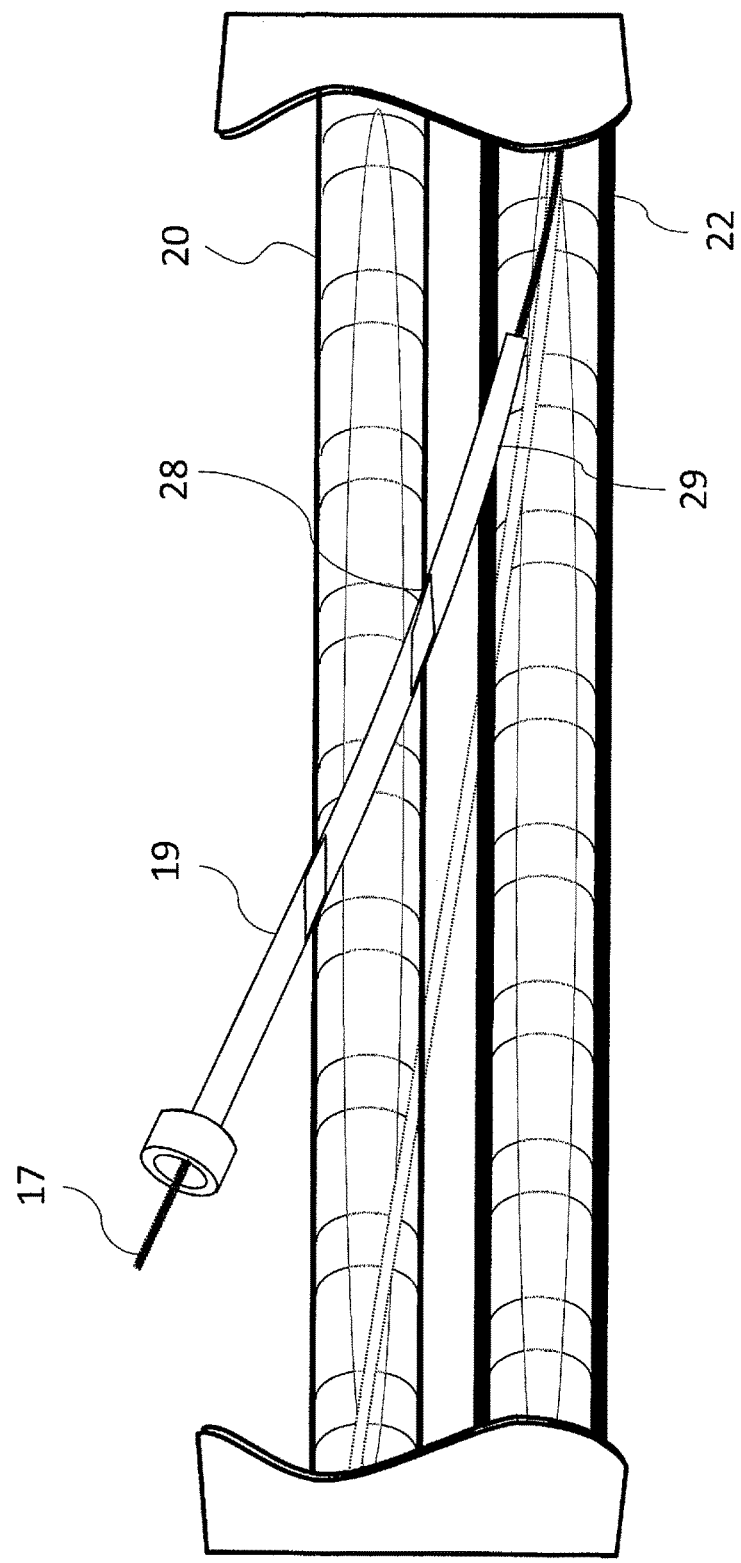

SYSTEMS AND METHODS FOR PERCUTANEOUS ACCESS AND FORMATION OF ARTERIOVENOUS FISTULAS

This application claims the benefit under 35 U.S.C. 119(e) of the filing date of Provisional U.S. Application Ser. No. 62/208,353, entitled Protected Distal Tip Systems and Methods, filed on Aug. 21, 2015, which application is expressly incorporated herein by reference, in its entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser approaches and a number of methods using various connected prostheses, clips, and stents.

An arterio-venous fistula (AVF) is created by connecting an artery to a vein, and to create a leak-free blood flow path between them. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with 1) catheters placed in large veins, 2) prosthetic grafts attached to an artery and a vein, or 3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialyzed and non-dialyzed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention eliminates the above described open procedures, reduces operating time, and allows for consistent and repeatable fistula creation.

The present invention comprises a device for creating a percutaneous arteriovenous (AV) fistula, which comprises a proximal base having a distal diagonal end surface and a distal tip connected to the proximal base and movable relative to the proximal base. The distal tip has a proximal diagonal end surface. A first heating assembly, comprising an embedded energized heating element, is disposed on at least one of the distal diagonal end surface and the proximal diagonal end surface. A second heating assembly, comprising a passive non-energized heat spreader, is disposed on the other distal diagonal end surface. The distal diagonal end surface and the proximal diagonal end surface are adapted to contact opposing sides of a tissue portion to create the fistula. The distal diagonal end surface is oriented at an angle of 15-90 degrees relative to a longitudinal axis of the device, and more advantageously at an angle of 15-50 degrees relative to the longitudinal axis. In one particularly optimal configuration, the distal diagonal end surface is oriented at an angle of approximately 23 degrees relative to the longitudinal axis. The angle of the proximal diagonal end surface matches the angle of the distal diagonal end surface, so that the two surfaces match one another while working on opposite sides of the tissue.

A shaft is provided for connecting the distal tip to the proximal base, the shaft being extendable and retractable to extend and retract the distal tip relative to the proximal base. A resilient member in the distal tip manages pressure in the weld.

The proximal diagonal end surface has an embedded heating element disposed thereon. An energized heating element optimally comprises a serpentine configuration within a thermally conductive material. A temperature sensor is disposed near the energized heating element within the conductive material, for providing closed loop temperature control to the heater.

The heat spreader on the proximal face of the distal tip comprises a thermally conductive material which extends across a substantial portion of the diagonal end surface on which it is disposed, the heat spreader being in thermal contact with the energized heating element to conduct heat from the heating element and spread the heat across the diagonal end surface. It is constructed so that it has a thickness approximately equal to a thickness of a vessel in which the device is deployed, this thickness falling within a range of 0.010 inches to 0.060 inches. This is done for optimum radial conduction of heat into tissues. Other configurations optimize heat spreader thickness for insertion. In this application, a smaller profile is desired.

In one configuration, the heat spreader comprises a raised segment forming a rib, for creating a focused heat conduction path through tissue which will quickly cut or ablate tissue. This creates the opening in the fistula through which the blood will flow. After creating the opening, raised segment contacts the heat spreader on the opposing diagonal surface to heat said spreader up to a welding temperature. The tissue between the spreaders are then held at temperatures and pressures required to fuse the tissues together.

The distal tip comprises a distal diagonal outer surface containing an aperture for a through lumen for receiving a guidewire. The distal diagonal surface and the diagonal heat spreader surface are connected with a resilient media which maintains the appropriate pressure for tissue welding.

A position sensor is provided for monitoring movement of the distal tip with respect to the proximal base. This relative position indicates the thickness of tissue captured prior to fistula creation. This information can be valuable in determining if the procedure is proceeding properly. Vessel wall thicknesses are seen on ultrasound and can be estimated. This vessel wall thickness should be reflected in the position sensor. When cutting through tissue, the position sensor should indicate when the tissues are penetrated.

In another aspect of the invention, there is provided a method for creating an arteriovenous (AV) fistula, which comprises steps of selecting an appropriate procedural site having each of a primary vessel and a secondary vessel in close proximity to one another, inserting a piercing device into the primary vessel to pierce the vessel walls, and creating an opening so that the piercing device extends into the adjacent secondary vessel, and advancing a guidewire until the guidewire is positioned in a blood flow path of the secondary vessel sufficiently to allow the piercing device to be removed. The piercing device is then withdrawn. A proximal end of the guidewire is loaded into the distal lumen of a device for dilating the guidewire's path through both vessels. The proximal end of the dilator is then loaded into the lumen of a sheath and advanced through both vessels. The dilator is then removed and replaced by the device. The distal tip of the device is then advanced to place the proximal and distal diagonals in the first and second vessels. The sheath is then removed so that the proximal and distal diagonal jaw faces directly oppose the first and second vessel walls.

At this juncture, a heater on the diagonal distal surface of the proximal base is seated against an inner wall of the first vessel surrounding the opening. The distal tip is retracted so that the heat spreader on the diagonal proximal surface of the distal tip seats against an inner wall of the second vessel surrounding the opening, thereby capturing the walls of the first and second vessel between the facing angled surfaces of each of the distal tip and the proximal base, respectively.

The distal tip and the proximal base are pulled together, and at the same time energy is applied to the heating element on the distal diagonal surface of the proximal base. The resultant applied heat and motion causes the raised rib on the heater to cut or ablate through tissue until the raised rib contacts the heat spreader on the distal tip. The raised rib allows tissue to reside between the embedded heater and the heat spreader. The proximal heater transfers heat to the distal heat spreader by direct conduction from the contact of the raised rib with the distal heat spreader The distal heat spreader floats on a resilient base contained within the tip while in contact with the proximal heater. Sufficient energy is applied to weld tissue. The device is then removed leaving a welded fistula with blood flow sufficient to support dialysis.

In still another aspect of the invention, a method of creating a passage between adjacent primary and secondary vessels is disclosed, comprising a step of positioning a sheath across both vessels at the fistula site, introducing the device into the sheath so that its distal mechanisms are placed appropriately in relation to the vessel walls, removing the sheath, actuating a cutting mechanism in the device to open a communicating aperture from the primary to secondary vessel, and actuating a welding mechanism in the device to weld both vessels together.

In yet another aspect of the invention, there is provided a catheter system for creating an arteriovenous (AV) fistula, which comprises a proximal base having a distal diagonal end surface and a distal tip connected to the proximal base and movable relative to the proximal base, wherein the distal tip has a proximal diagonal end surface The distal diagonal end surface and the proximal diagonal end surface are each adapted to contact opposing sides of a tissue portion to create the fistula. A peripheral edge defines the proximal distal end surface. A proximal point is disposed on the peripheral edge. Advantageously, the proximal point comprises a shortened angle and a fully radiused edge relative to a remaining portion of the peripheral edge.

Another advantageous feature of the present invention is the provision of a relief recess disposed on a distal end of the proximal base. The catheter system is disposed along an operating axis and the relief recess is peripherally spaced from the proximal point on an opposed side of the axis relative to the proximal point. When a sheath is disposed about the proximal base, the sheath having a distal end wherein a portion of the sheath distal end is disposed on the relief recess, a space is created at another peripheral portion of the sheath distal end into which the proximal point may pass, thereby minimizing the chance that the proximal point will snag adjacent tissue.

Yet another advantageous feature of the invention is the provision of a stop formed in a peripheral edge of the distal diagonal end surface of the proximal base, the stop being disposed at a peripheral location directly aligned with the proximal point, so that the stop will engage the proximal point to prevent tissue snagging.

A shaft is provided for connecting the distal tip to the proximal base, the shaft being extendable and retractable to extend and retract said distal tip relative to the proximal base. Additionally, a heating assembly comprising an energizable heating element is disposed on at least one of the distal diagonal end surface and the proximal diagonal end surface.

In still another aspect of the invention, there is provided a catheter system for creating an arteriovenous (AV) fistula, which comprises a proximal base having a distal diagonal end surface and a distal tip connected to the proximal base and movable relative to the proximal base. The distal tip has a proximal diagonal end surface. The distal diagonal end surface and the proximal diagonal end surface are adapted to contact opposing sides of a tissue portion to create the fistula. Advantageously, a relief recess is disposed on a distal end of the proximal base.

The catheter system may further comprise a peripheral edge defining the proximal distal end surface and a proximal point on the peripheral edge. The catheter system is disposed along an operating axis and the relief recess is peripherally spaced from the proximal point on an opposed side of the axis relative to the proximal point. A sheath is disposed about the proximal base, the sheath having a distal end wherein a portion of the sheath distal end is disposed on the relief recess, wherein a space is created at another peripheral portion of the sheath distal end into which the proximal point may pass.

A stop may be formed in a peripheral edge of the distal diagonal end surface of the proximal base, the stop being disposed at a peripheral location directly aligned with the proximal point. A shaft for connecting the distal tip to the proximal base is provided, the shaft being extendable and retractable to extend and retract the distal tip relative to the proximal base. A heating assembly comprising an energizable heating element may be disposed on at least one of the distal diagonal end surface and the proximal diagonal end surface.

The invention, together with additional features and advantages thereof, may best be understood by reference to the following description taken in conjunction with the accompanying illustrative drawings.

BRIEF DESCRIPTION OF THE DRAWINGS

FIG. 1a is an elevational view of the handle portion of a device constructed in accordance with one embodiment of the present invention;

FIG. 1b is an elevational enlarged view of the circled distal working portion of the device of FIG. 1a;

FIG. 6 is an isometric view of the distal tip;

FIG. 7c is a diagram depicting the insertion of the sheath into vessels;

DETAILED DESCRIPTION OF THE INVENTION

Notation and Nomenclature

Figure 2A:
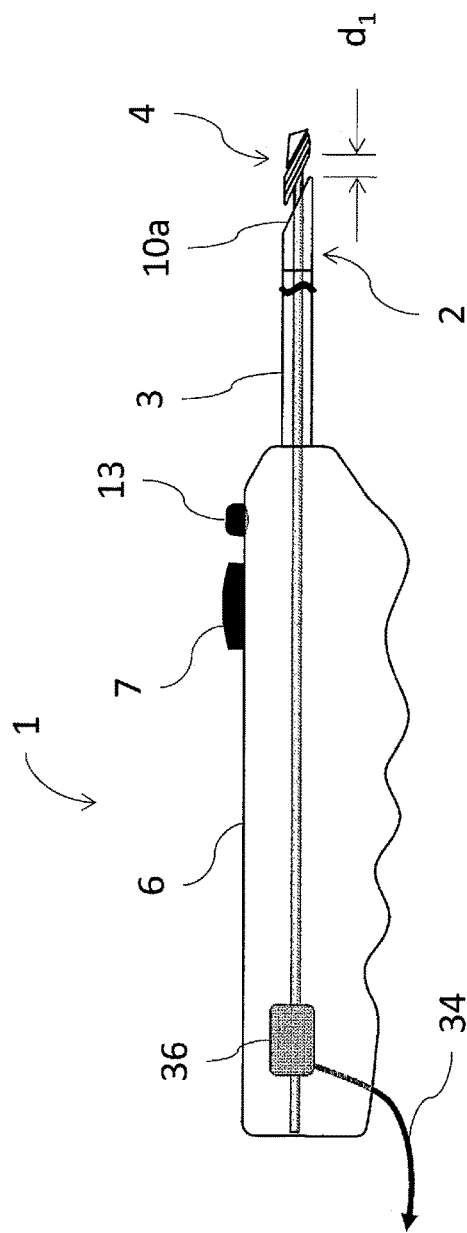
FIG. 2a is an elevational view of an embodiment like that shown in FIGS. 1a-1b, with the distal end in a first working configuration.

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. Further, the terms "proximal" and distal are intended to refer to proximity relative to a bone anchor applicator. Thus, if a first device is distal and a second device is proximal, the second device is nearer to the bone anchor applicator than the first device.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent application and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein. The technology disclosed herein would have a broad application in vessel surgery for an animal, such as a human. This includes surgery of ducts, ureters, arteries, veins, grafts, or any other tubular structure that transports material. Some of these procedures include, but are not limited to, artery to venous fistula creation, vascular repair, coronary artery bypass graft surgery, femoral popliteal bypass, transjugular intrahepatic portosystemic shunt, splenorenal shunt, or a mesocaval shunt.

Referring now more particularly to the drawings, as illustrated in FIGS. 1a and 1b, one embodiment of the inventive intraluminal anastomotic device 1 comprises a catheter 1a, including a proximal heating assembly 2, a proximal shaft 3, a distal heating assembly 4, and a handpiece 6. The distal heating assembly 4 comprises a distal tip 5 and heat spreader 24. The handpiece 6 comprises a tip actuation button 7 and a release button 13. The proximal heating assembly 2 is constructed of a proximal base 10 that is cut at an angle θ at the distal end.

On the diagonal surface 10a of the proximal base 10, a heating element 8 is embedded. The proximal base 10 is typically constructed of a thermally insulating material that is resistive to high temperatures. An embedded heater 12 is used to compress and heat the tissue to create coaptation of vessel tissues. This process is known as tissue welding or tissue fusion. In one embodiment, the embedded heater 12 is constructed of a thermally conductive material with the resistive heating element embedded therein.

Figure 4B:
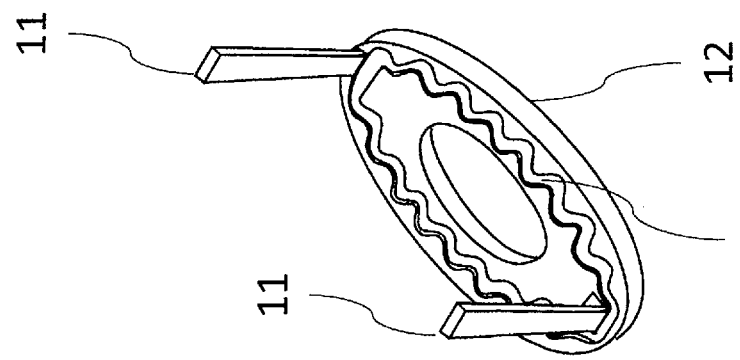
FIG. 4b is an isometric view showing the embedded heater.
Figure 4A:
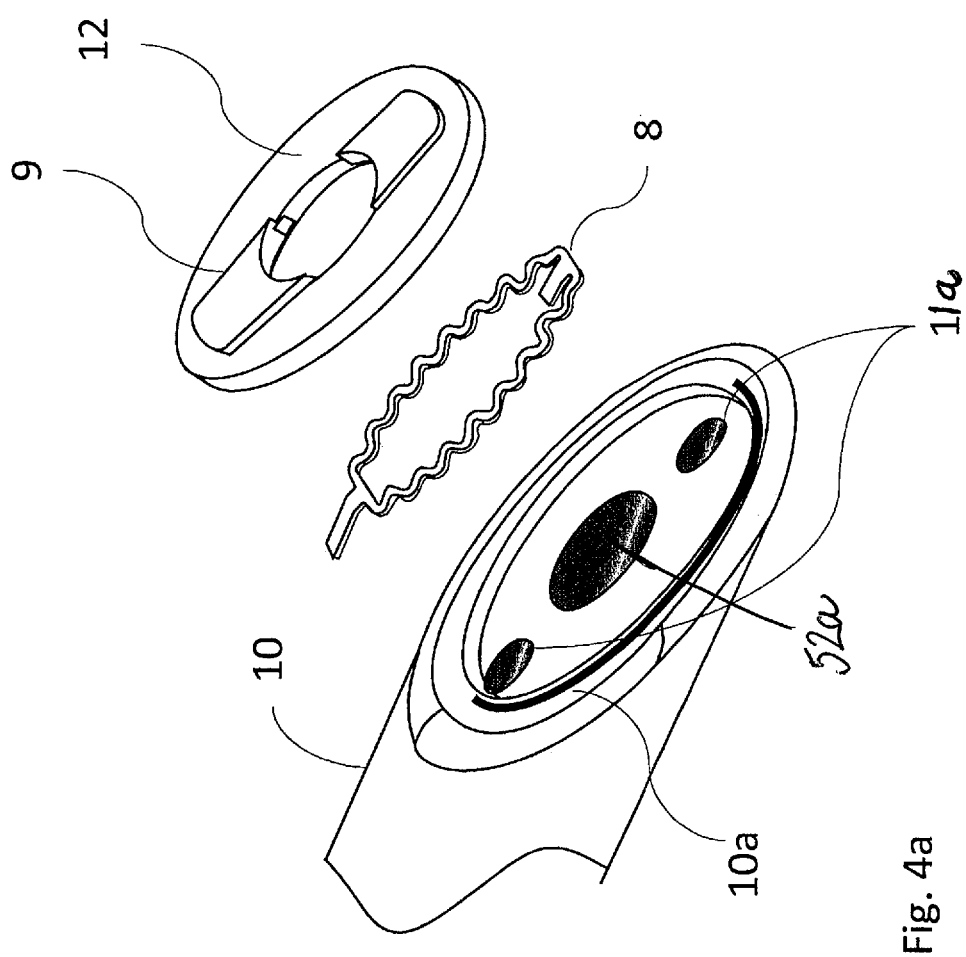
FIG. 4a is an exploded isometric view illustrating an embodiment of the proximal base and particularly showing the assembly of the embedded heater.
Figure 5:
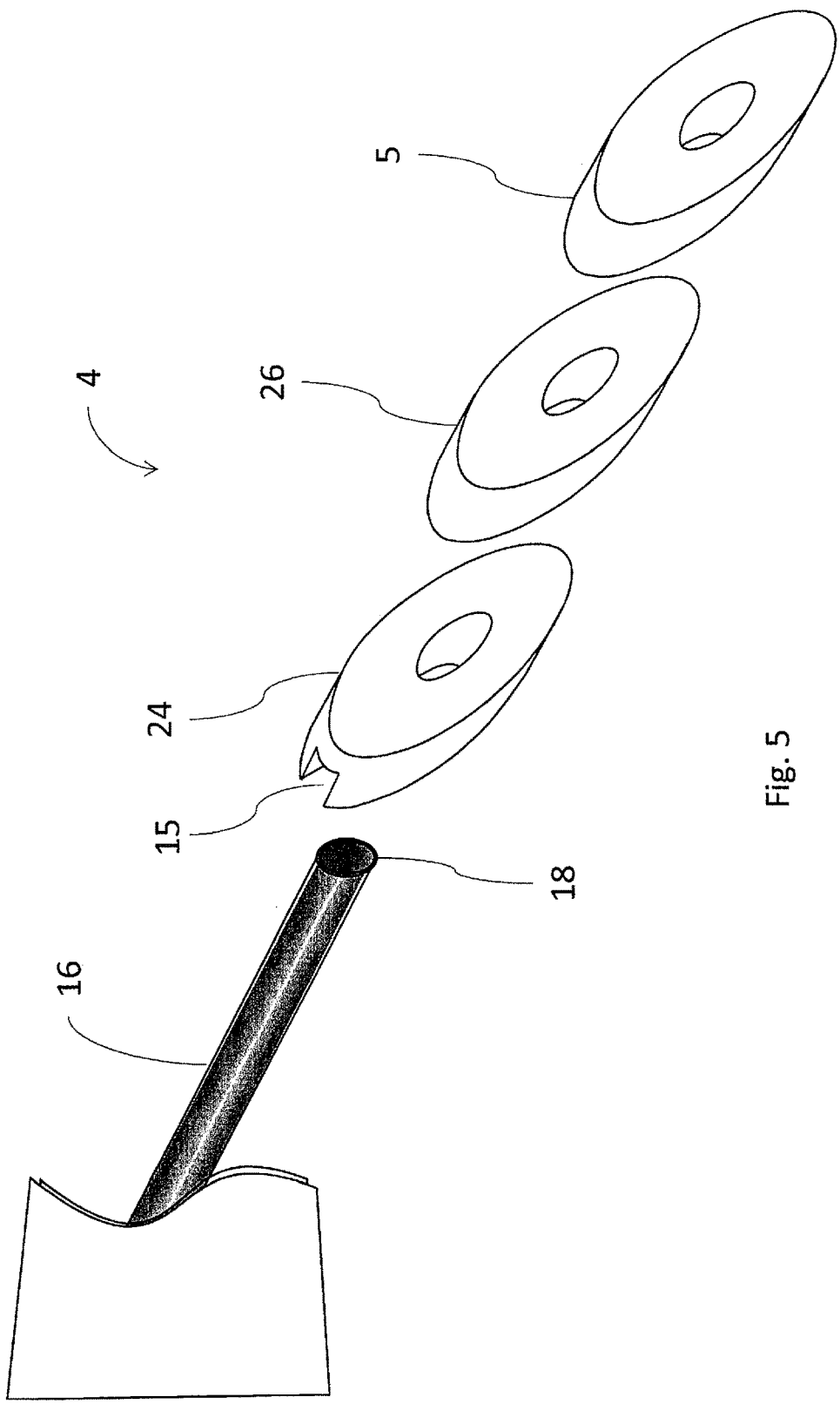
FIG. 5 is an exploded isometric view of the distal tip showing the heat spreader, the resilient member, and the guidewire lumen.

FIG. 4a and FIG. 4b show the construction of embedded heater or heating surface 12. Heating element 8 takes on a serpentine configuration to increase length and, therefore, surface area leading to higher energy densities. Heating element 8 is attached inside of a mating cavity from which power attachment leads 11 extend and are inserted into lumens 11a where they are attached to conductors that extend back to handpiece 6. Ribs 9 are a part of embedded heater 12 and are also made of a conductive material. Ribs 9 will heat up to initially cut tissue prior to welding. Ribs 9 move into rib relief 15 on heat spreader 24 to cut tissue (see FIG. 5).

Figure 9:
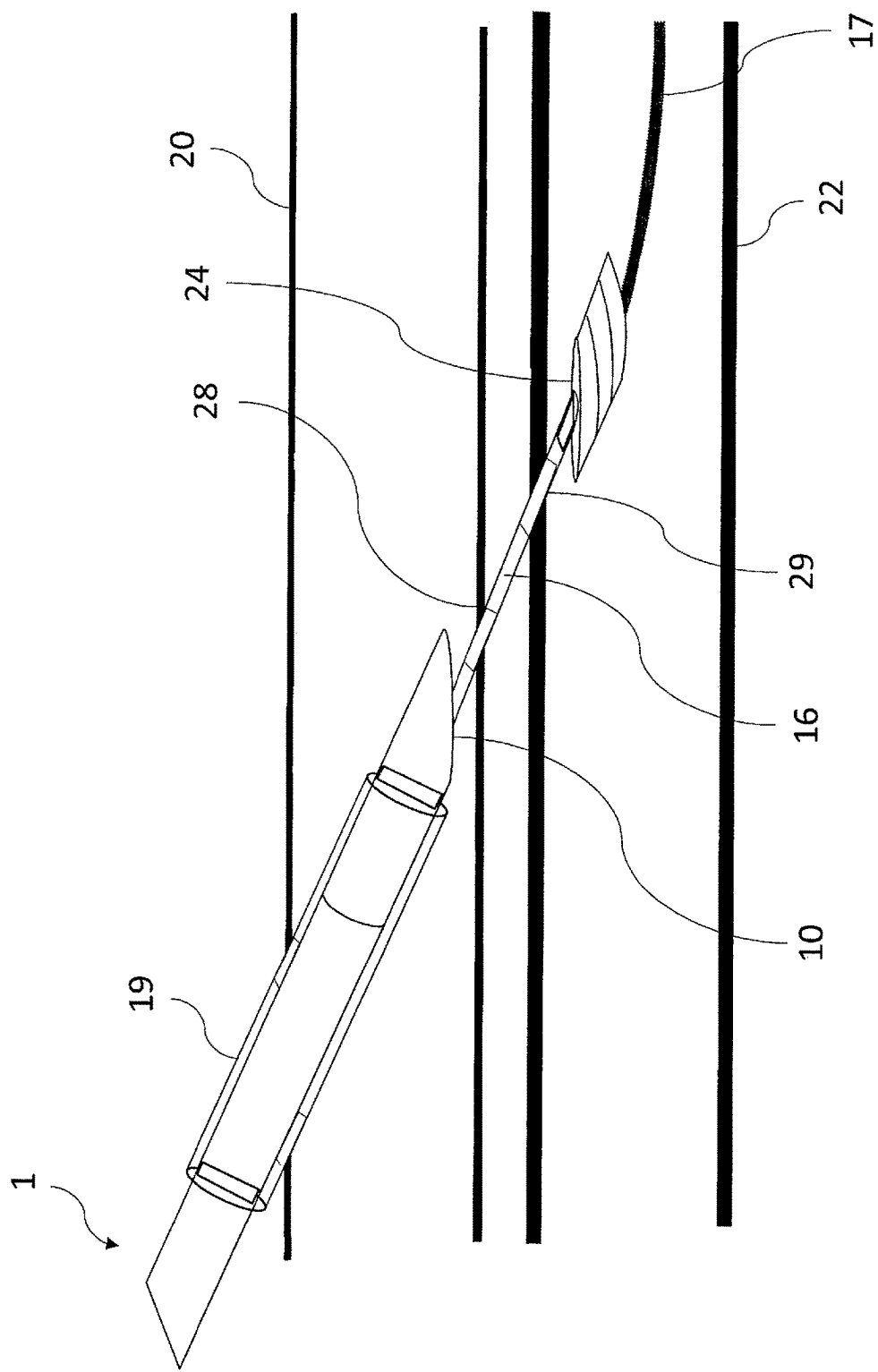
FIG. 9 is a diagram depicting the retraction of the sheath and placement of the device within vessels.

The proximal base 10 is configured with at least one thermocouple or temperature sensor 14 shown in FIG. 1b to monitor the temperature near the active heating element 8, and provides a means for closed loop temperature control to optimize tissue welding and cutting. The proximal base is designed to reside in primary vessel 20 (FIG. 9) during deployment.

Figure 2B:
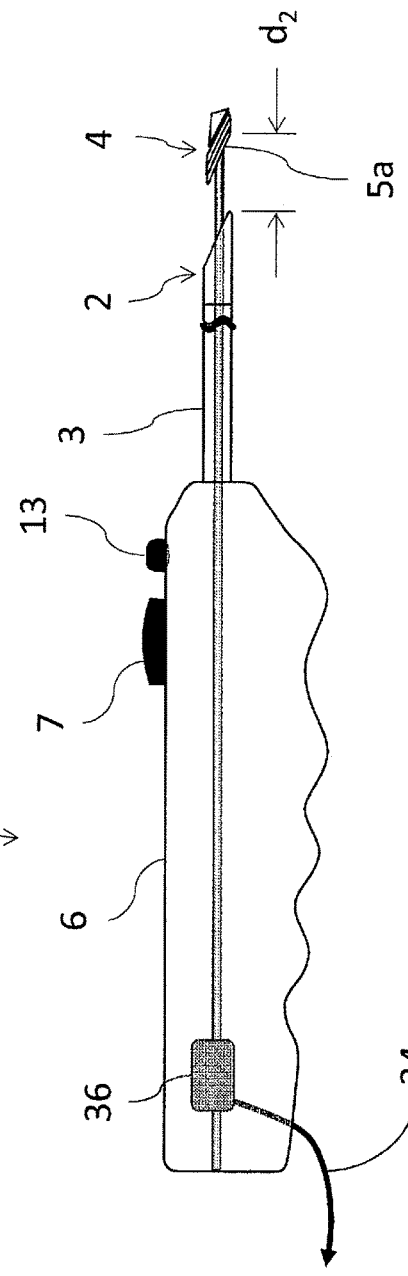
FIG. 2b is an elevational view similar to FIG. 2a, with the distal end in a second working configuration.
Figure 3:
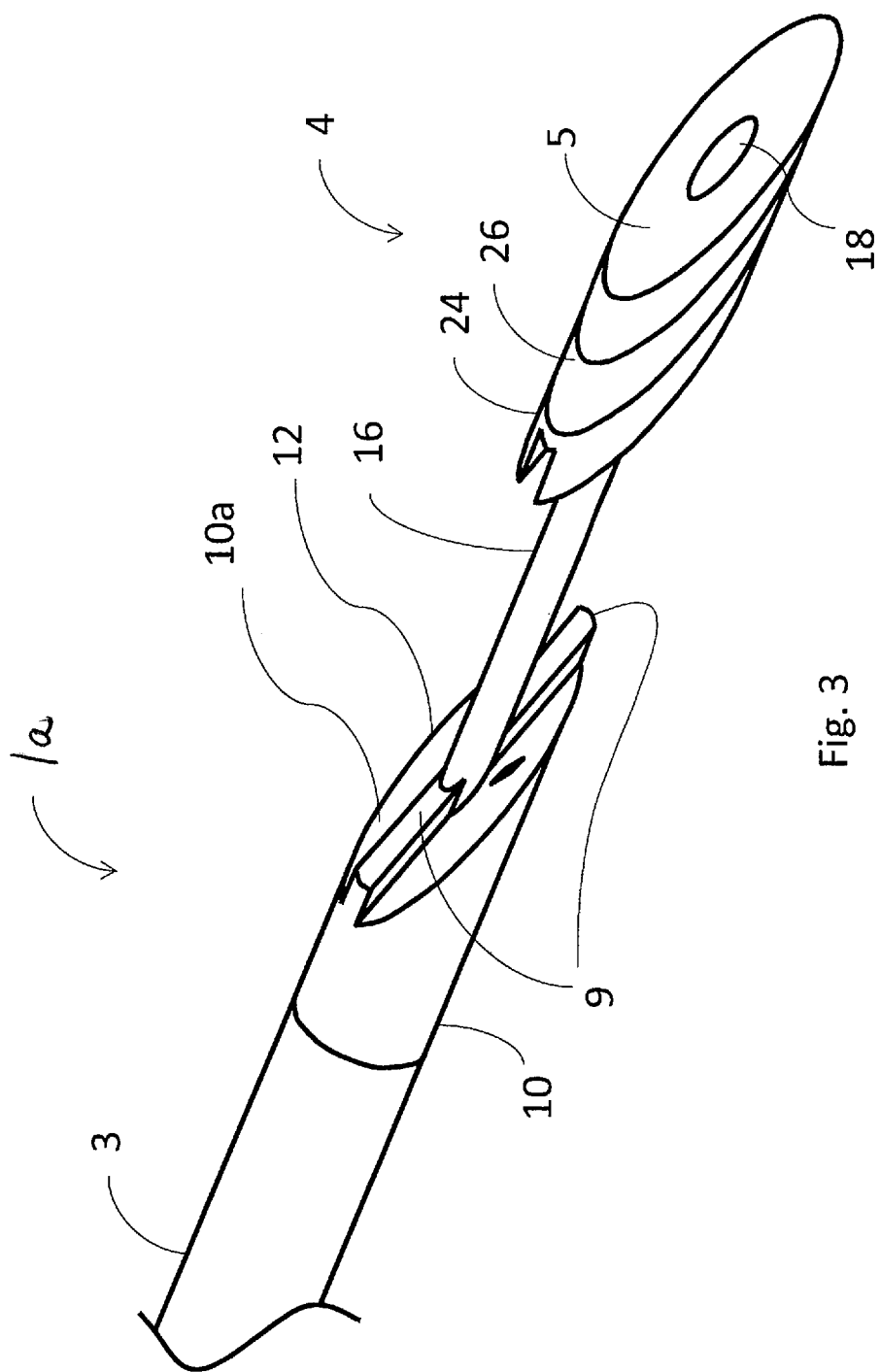
FIG. 3 is an isometric view of one embodiment of the device shown in FIGS. 1a-2b.

As illustrated in FIGS. 1-3, the distal tip 5 terminates in a diagonal surface at angle θ. A guidewire lumen 18 extends through the center of the distal tip 5, as shown in FIG. 3. Distal heating assembly 4 is designed to reside in secondary vessel 22 (FIG. 9) during deployment. Distal tip 5 moves with center shaft 16 to desired distance d as shown in FIGS. 2a and 2b. Movement is generally to bring distal tip 5 toward the proximal heating assembly 2, thereby capturing vessel wall tissues between the two components 2 and 4 for the purpose of welding said tissues together. A proximal end surface 5a of the distal heating assembly 4 is angled to precisely match the angle θ of the proximal heating assembly 2. This is designed so that components 2 and 4 capture vessel tissue between parallel surfaces.

Figure 12:
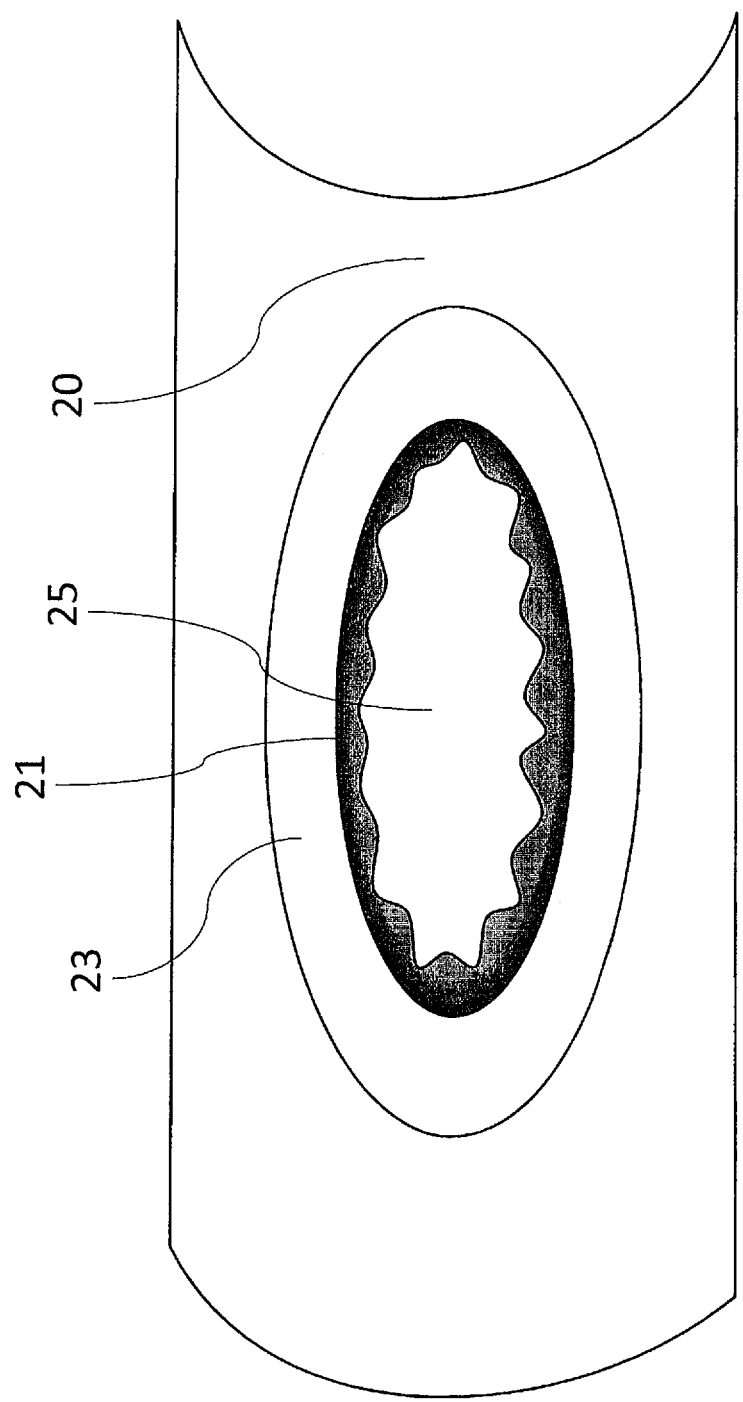
FIG. 12 is a diagram of an anastomosis creating using the devices and methods disclosed in the present application.

The proximal base 10 is configured as shown in FIGS. 4a and 4b. The proximal base 10 is configured to receive heating element 8 (FIGS. 4a and 4b), which is covered by heating surface 12. The heating surface 12 is comprised of a thermally conductive material which draws heat from heating element 8. Power attachment points 11 ensure that heating element 8 may be energized. The heating surface 12 transfers heat into the adjoining vessels to create a weld and/or cut tissue to create an anastomosis or fistula 25 (FIG. 12). The size and shape of heating surface 12 mirrors the anastomosis to be created. The thickness of the heating surface 12 is approximately the thickness of the vessel in which the weld is being created. However, the thickness may be increased or decreased to control the amount of heat that is conducted into the surrounding tissue. Typical thickness of the heating surface ranges from 0.010 inches to 0.060 inches (FIGS. 3a-3b, 4a-4c).

The embodiment illustrated in FIGS. 2a and 2b provides distal tip feedback, wherein movement of the distal heating assembly 4, from $d_2$ to $d_1$, is converted to a signal by a position sensor 36 within the handpiece 6, or alternatively, outside of handpiece 6. This movement can then be displayed and/or utilized for a control algorithm. A signal that relays the absolute position of the distal heating assembly 4 from the position sensor 36 to a display device (not shown) of some type, through an output signal cable 34 is valuable for verifying the tip position throughout the procedure and for determining the thickness of the tissue between the tip and base of the catheter 1a before, during, and after the formation of the fistula 25 (FIG. 12). The tissue thickness is related to the distance measurement by the equation $T = d \sin θ$. The tissue thickness before the procedure can be correlated to the length of the fistula post-procedure. The relative position of the distal heating assembly 4 during the formation of the fistula 25 is also valuable and can be related to the rate of tissue dessication, cutting and welding. This signal may be used as an input to control heat application. For example, in FIG. 2*a*, the proximal heating assembly 2 and distal heating assembly 4 are spaced by a distance $d_1$, prior to the procedure. Based upon the type and thickness of the tissue through which the anastomosis is being created, and other factors related to functionality and durability of the fistula, tip position after the procedure can provide confirmation that the tissue was properly desiccated and both vessel walls have been cut. The position of the tip can be verified using the sensor(s) 36.

Referring now particularly to FIGS. 7*a* through 10, a method for using the device 1 will be described. To begin the inventive method of intravascular access and communication, the practitioner selects an appropriate procedural site having each of a primary vessel 20 and a secondary vessel 22 in close proximity to one another. In currently preferred approaches, the primary vessel 20 comprises a vein, and the secondary vessel 22 comprises an artery, but the invention is not limited to this arrangement. Initially, a piercing device is inserted into the primary vessel 20 and actuated to pierce the vessel walls and extend into the adjacent secondary vessel 22. Once penetration from primary vessel 20 to secondary vessel 22 has been achieved, guidewire 17 is advanced until positioned in the blood flow path of blood vessel 22 sufficiently to allow the piercing device to be removed while retaining the guidewire's position in blood vessel 22.

Figure 7A:
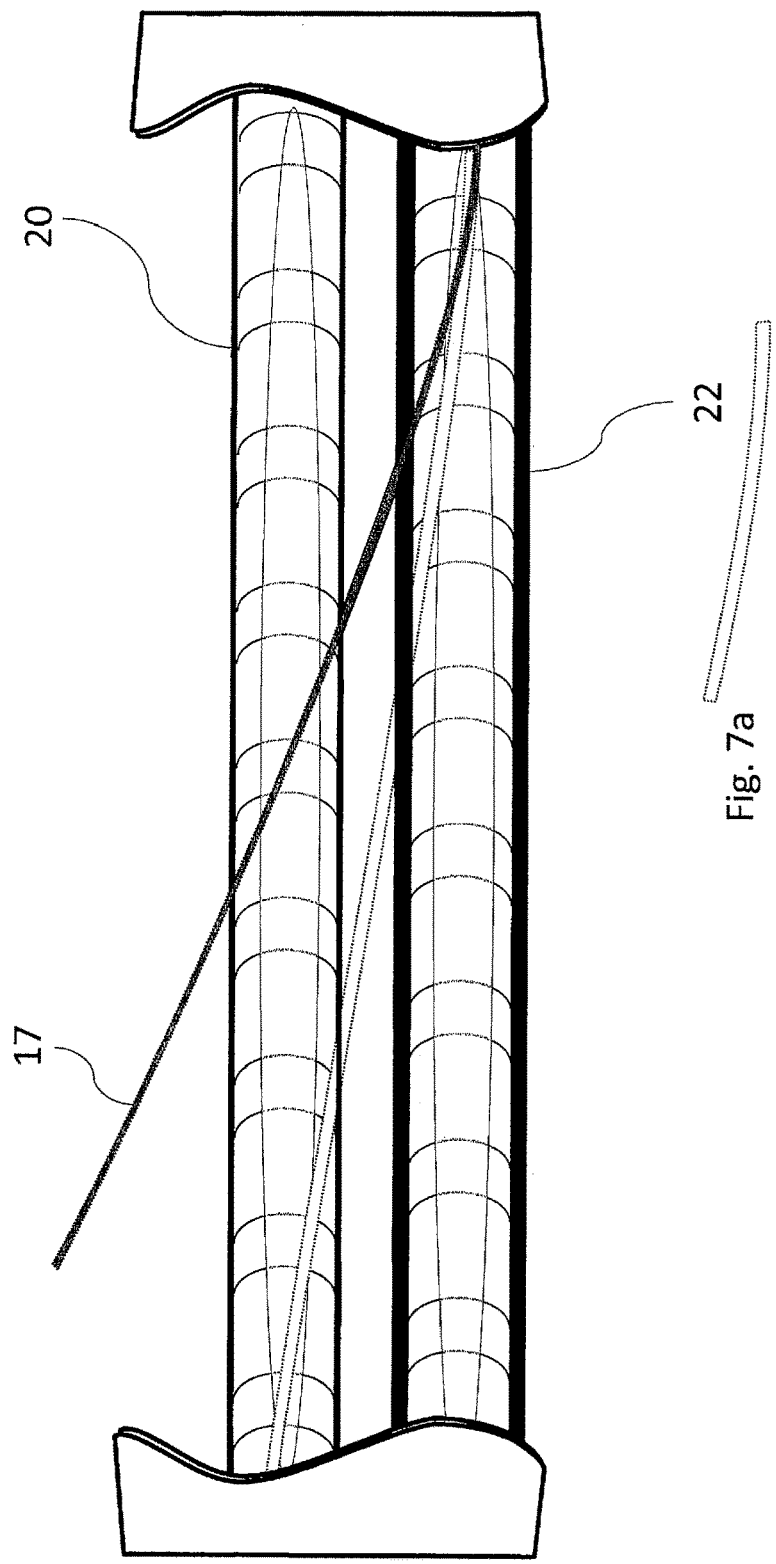
FIG. 7a is a diagram depicting the insertion of the guidewire into vessels.
Figure 13:
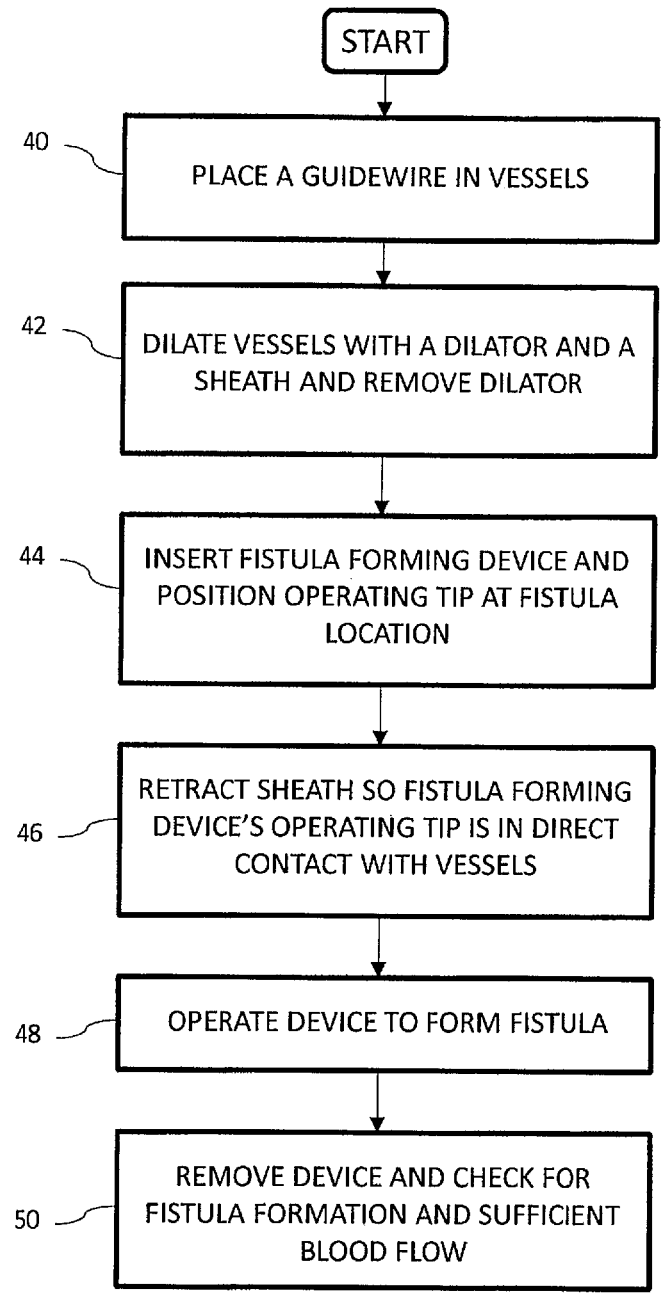
FIG. 13 shows a flow diagram of a medical procedure, using an AV fistula creating device according to at least certain embodiments.
Figure 14:
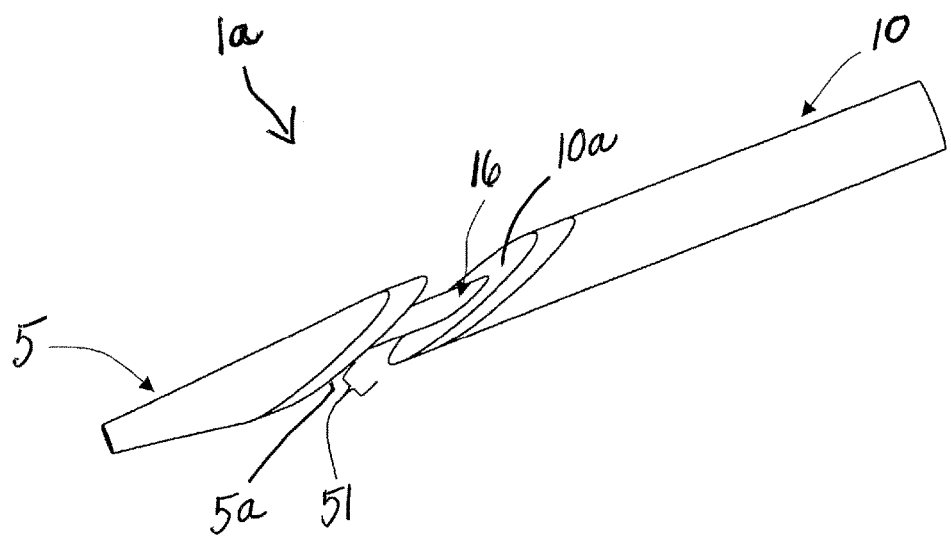
FIG. 14 is a view of a catheter which may be used in connection with the foregoing embodiments for compressing tissue.

Once guidewire 17 is sufficiently in position as shown in FIG. 7*a*, the practitioner withdraws the piercing device completely from the body, thus leaving the guidewire in the desired position and crossing from primary vessel 20 to secondary vessel 22 as shown in FIG. 7*a* and as described in block 40 of the flow chart illustrated in FIG. 13. One exemplary piercing system and methods is disclosed in co-pending U.S. application Ser. No. 13/668,190, commonly assigned with the present application, and expressly incorporated herein by reference, in its entirety, but any suitable piercing system and method may be used within the scope of the present invention.

Figure 7B:
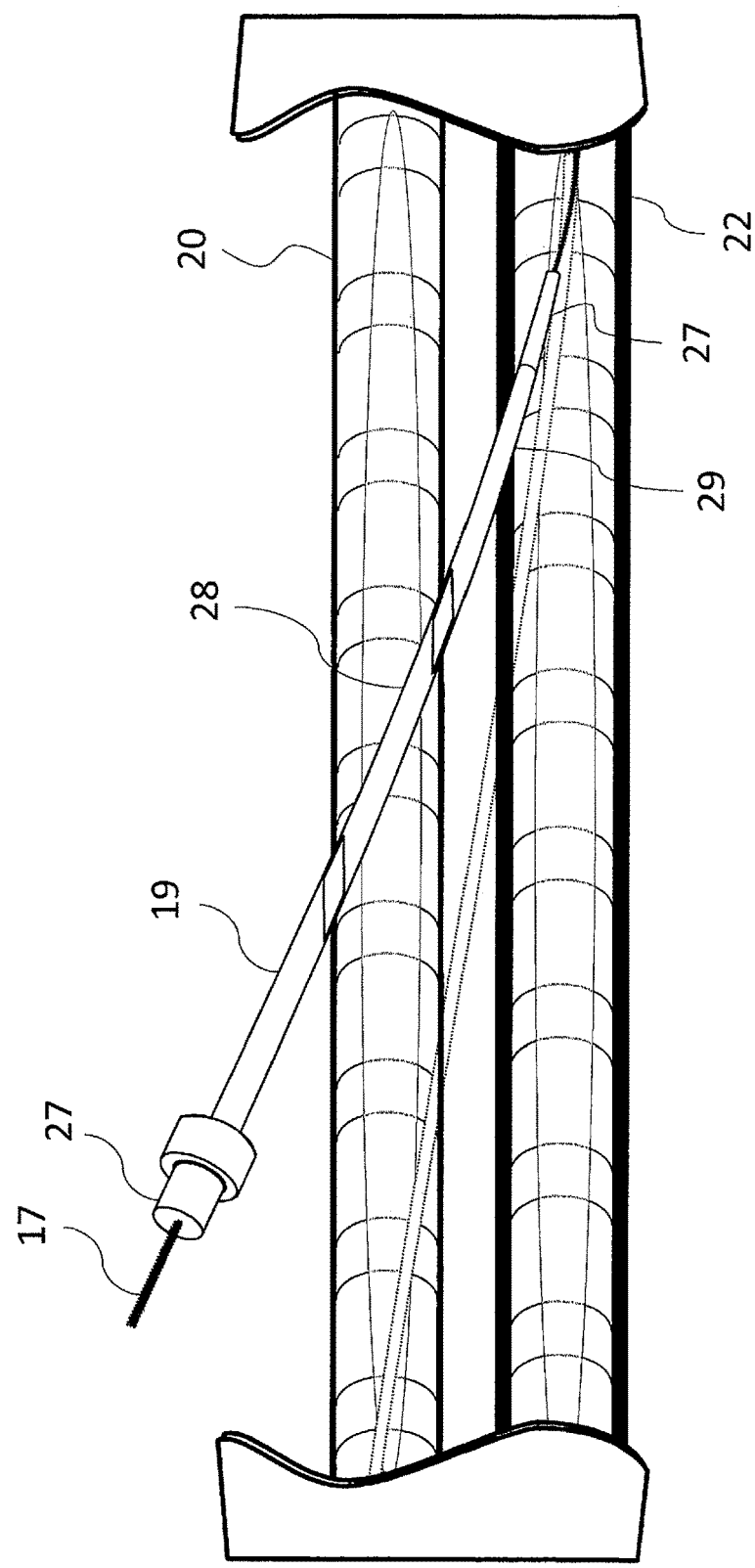
FIG. 7b is a diagram depicting the insertion of the dilator into vessels.
Figure 8:
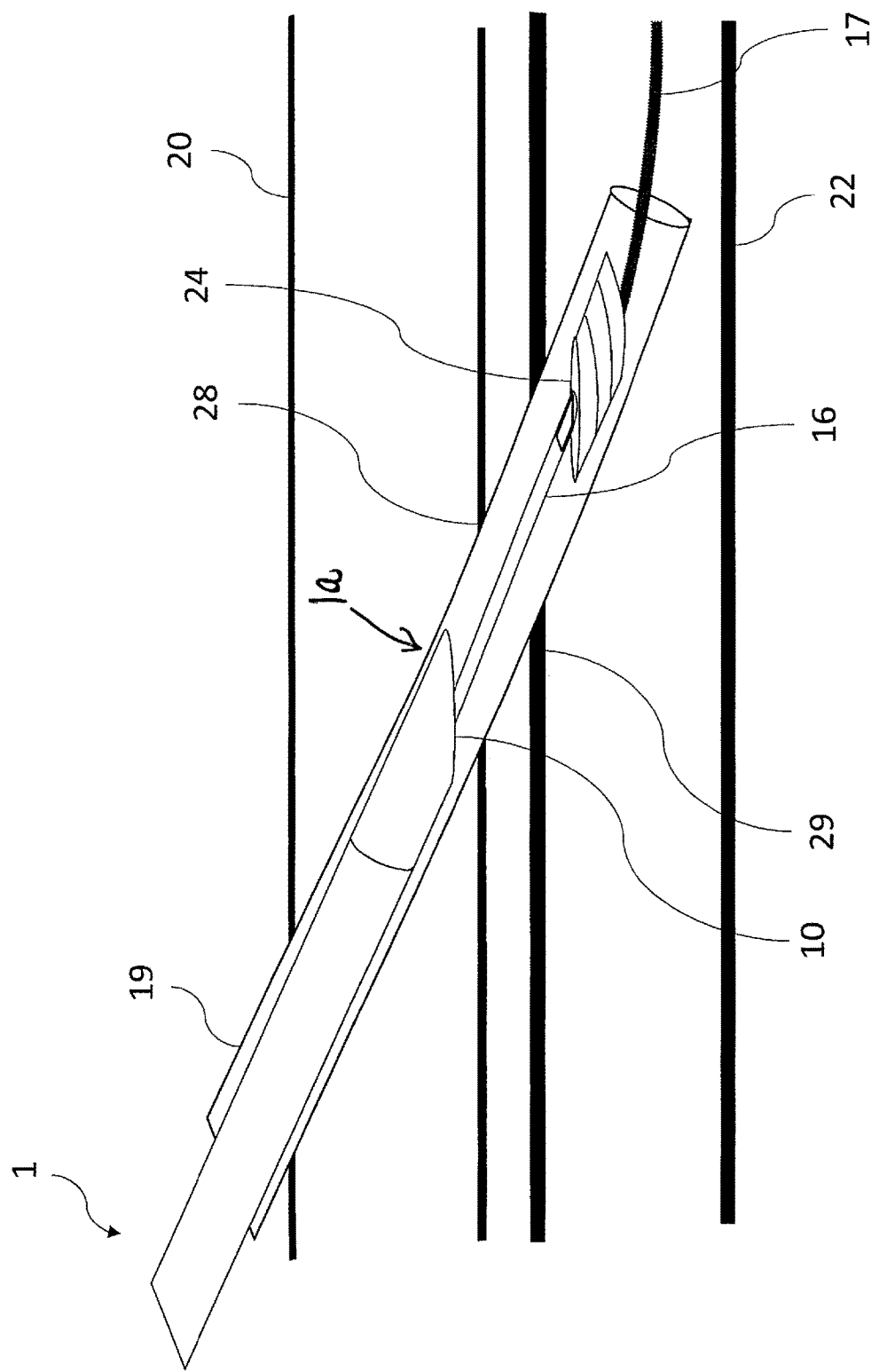
FIG. 8 is a diagram depicting the insertion of the device into the sheath.

Guidewire 17 now provides a track over which the rest of the procedure is performed. First and second vessel openings 28 and 29, respectively must be dilated so that a sheath 19 (FIG. 7*b*) and device 1 may have access. FIG. 7*b* shows a dilator 27 advancing over guidewire 17 to dilate vessel 20 at opening 28 and vessel 22 at opening 29 in anticipation of needing these openings to advance sheath 19 and finally device 1.

Creating openings 28 and 29 in the blood vessels 20 and 22 is a step that is carefully engineered. The tortuosities involved in device access across openings 28 and 29 mandate that both of the dilator 27 and the sheath 19 be made of flexible materials. These tortuosities are further complicated by the need for tapers on the dilator 27 and sheath 19 to be long. Openings 28 and 29 in vessels need to be created in such a way that there are no tears.

Tears in openings 28 and 29 will immediately start to bleed. Blood that enters the fistula site will affect the patency of the tissue weld. Blood needs to stay out of the extra-vessel welding site. Tears created at this point will have minutes to bleed into the extra-vessel space until the procedure advances to tissue welding.

Tears can also cause openings 28 and 29 to not seal sufficiently by device 1. To make openings 28 and 29 without tears, tapers need to be long, smooth, lubricious and, importantly, un-interrupted.

Figure 10:
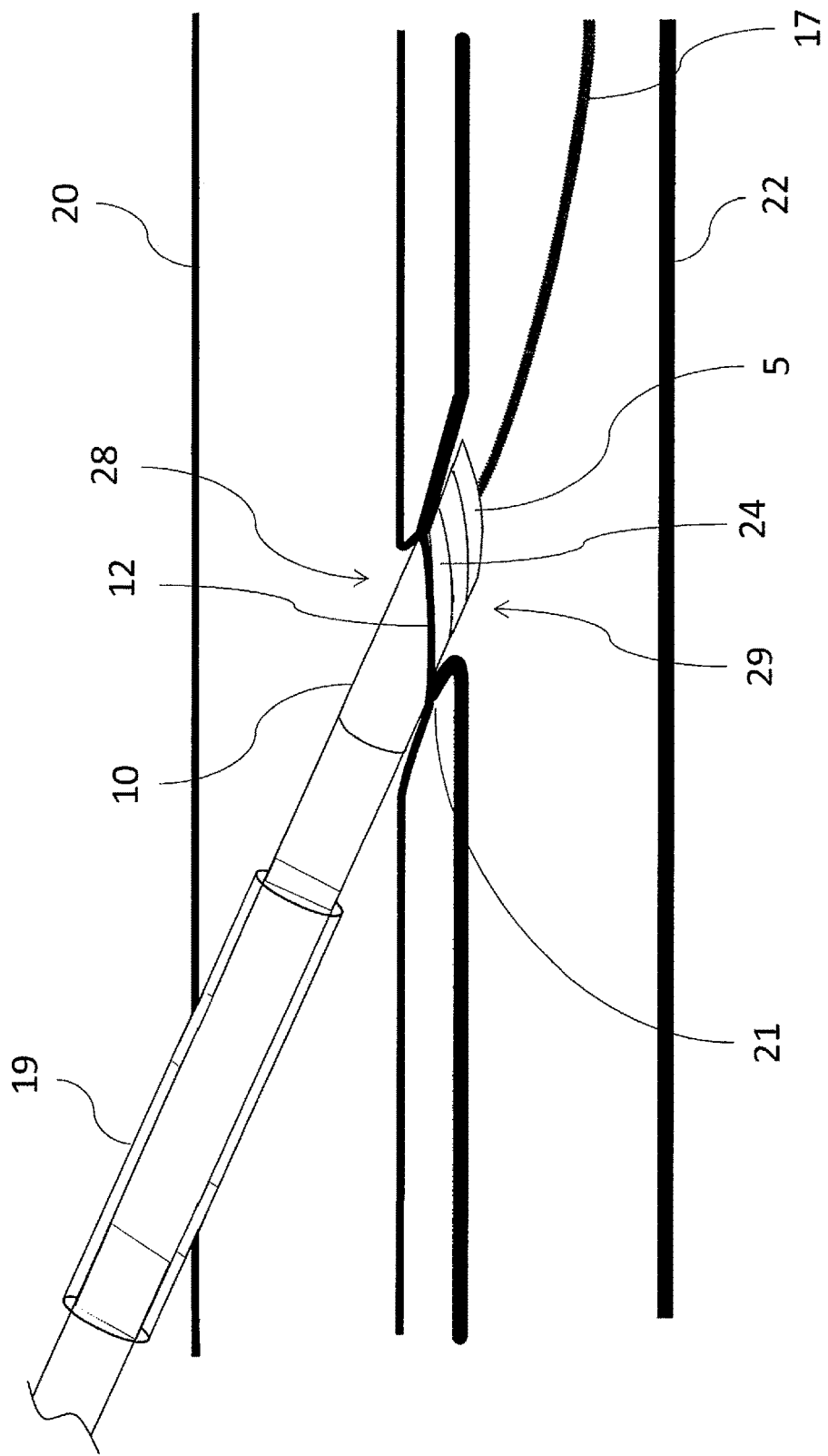
FIG. 10 is a diagram depicting the placement of the device with respect to vessels during welding and cutting.

Devices with tapered tips may also heat up part of their tip in the tissue welding. This, with the combined aggravation of interrupting the blood flow, does cause blood to coagulate within the vessel. The shorter the tip, the less coagulating affects the device during the procedure. It is because of this dynamic that device 1 is shown to have a blunt tip, although variable lengths and tapers can be used to accommodate variable vessel size. As can be seen in FIG. 10, the blunt profile is less intrusive to blood flow.

The inventive method of fistula creation continues with the advancement of sheath 19 as shown in FIG. 7*c* and as described in block 42 of FIG. 13. Sheath 19 is preferably a design with a very thin wall that continuously tapers to a cross-sectional dimension of nearly nothing at its distal tip. It is also very lubricious. Terumo's 6F Radial Artery Sheath "Glide Sheath Slender" is an exemplary example. Such a sheath can, in concert with an appropriate dilator, dilate a vessel wall while imparting minimal stress to the dilated tissues. This is important in that it minimizes tearing and also maximizes tissue recovery.

Room is then created for device 1 inside of sheath 19 by the removal of dilator 27 and as described in block 42 of FIG. 13. Guidewire 17 may or may not be removed at this point as well. This is a safety issue left up to the practitioner. Device 1 is then inserted into the patient by loading into the proximal end of sheath 19 and optionally over guidewire 17. The device 1 is advanced further into the patient until center shaft 16 is centered at the anastomosis site as in FIG. 8 and as described in block 44 of FIG. 13.

Ultrasound and/or fluoroscopy is used at this point to determine where tube 16 is relative to vessels 20 and 22. Ultrasound doesn't have the resolution and depth to indicate where the vessel walls are in relation to the embedded heater 12 face and heat spreader 24 faces. Manipulation of the device without a sheath can unknowingly move vessels around and actually get them intertwined and folded around device 1, especially around tube 16 and the proximal edge of heat spreader 24. These dynamics are hard to track under ultrasound and may go unnoticed. Proceeding with the cutting and welding on such unorganized tissue does not produce a viable fistula.

Because sheath 19 and dilator 27 do not disrupt vessels 20 and 22, this alignment is easier to approximate while device 1 is inside sheath 19. Alignment with the sheath in place avoids moving vessels around with device 1, as it is isolated from the vessels by the sheath. Adjustments to the relative placement of device 1 with vessels 20 and 22 do not move vessels 20 and 22 and are, therefore, not stressed. Less movement of the vessels, especially at openings 28 and 29, mean less stress imparted on the vessel openings. This minimizes tearing and maximizes elastic recovery and promotes improved coaptation for welding and cutting. The method of fistula creation continues by retracting sheath 19 and as described in block 46 of FIG. 13. Because sheath 19 has a very lubricious un-interrupted tapering outer surface, it can be removed without disturbing the alignment of center shaft 16 to the fistula site. Vessel openings 28 and 29 have not been overly stressed and elastically recover to seal around center shaft 16. A slight tension is applied to the embedded heater 12 to seat it against the vessel wall and promote vessel apposition. The blunt shape of the heat spreader 24 on the distal tip 5 prevents the distal tip from inadvertently retracting back through the vessel wall. The heat spreader 24 of the distal heating assembly 4 is then retracted to close the spacing between until the walls of the first and second vessels 20 and 22, respectively, are captured between the facing blunt surfaces of embedded heater 12 and distal heat spreader 24.

The method of fistula formation continues, as described in block 48 of FIG. 13, by applying a controlled tension between distal tip 5 and proximal base 10, and at this juncture, with the vessels securely clamped, energy is applied to proximal heating element 8. As embedded heater 12 heats up, rib 9 cuts through the vessel walls and embedded heater 12 will contact heat spreader 24. When fully retracted, the system is designed so that the two heating elements come into direct contact with one another to ensure a complete cut and capture of the vessel tissue.

Fistula formation continues, as described in block 48 of FIG. 13. After vessel walls are cut, rib 9 now contacts heat spreader 24 to conduct heat into the spreader for the purposes of welding the vessels together. Rib 9 floats inside of the rib relief 15 on heat spreader 24. Heat spreader 24 is spring loaded by both resilient member 26 (FIG. 1b) and spring tension on center shaft 16 to ensure proper pressures are maintained for tissue welding. Two springs are desirable because of the uncertain forces transmitted through tube 16. Tube 16 has high normal frictional forces imposed by angle θ which can be influenced by the variable coefficient of friction between tube 16 and proximal shaft 2. This coefficient of friction will change based on fluids within the fistula, tolerances within device 1, and the progress of coagulation of blood within the interface. This friction can vary by as much as a factor of 8. Resilient member 26 acts directly on the tissue interface with no frictional interference. This enables better assurance that the proper pressures are imparted on the tissues while welding.

Regarding the tissue welding process, more particularly, the DC resistive energy functions to fuse or weld the vessels together, creating an elongate aperture 25 (FIG. 12) through the opposing walls of each of the first and second vessels, as well as any intervening tissue. As formed, the elongate aperture may typically resemble a slit. However, as pressurized flow begins to occur through aperture 25, which creates a communicating aperture between the first and second blood vessels, the aperture widens in response to the pressure, taking the shape of an ellipse as it opens to form the desired fistula. The effect is illustrated in FIG. 12. The edges 21 of the aperture are cauterized and welded. Outwardly of the weld band 21 is a coaptation area 23. As shown, the cut area corresponds to the shape of the heating or cutting element. It can be of multiple shapes, such as round, oval, a slit, or a combination as shown. The area adjacent to the cut has been approximated and welded due to the flat face of the catheter 1a in the vein (first vessel) being larger than the embedded heater 12. The heat from the embedded heater 12 is also preferably spread over this area by a conductive material that can be above, below or within the embedded heater 12 or base 10.

Figure 11:
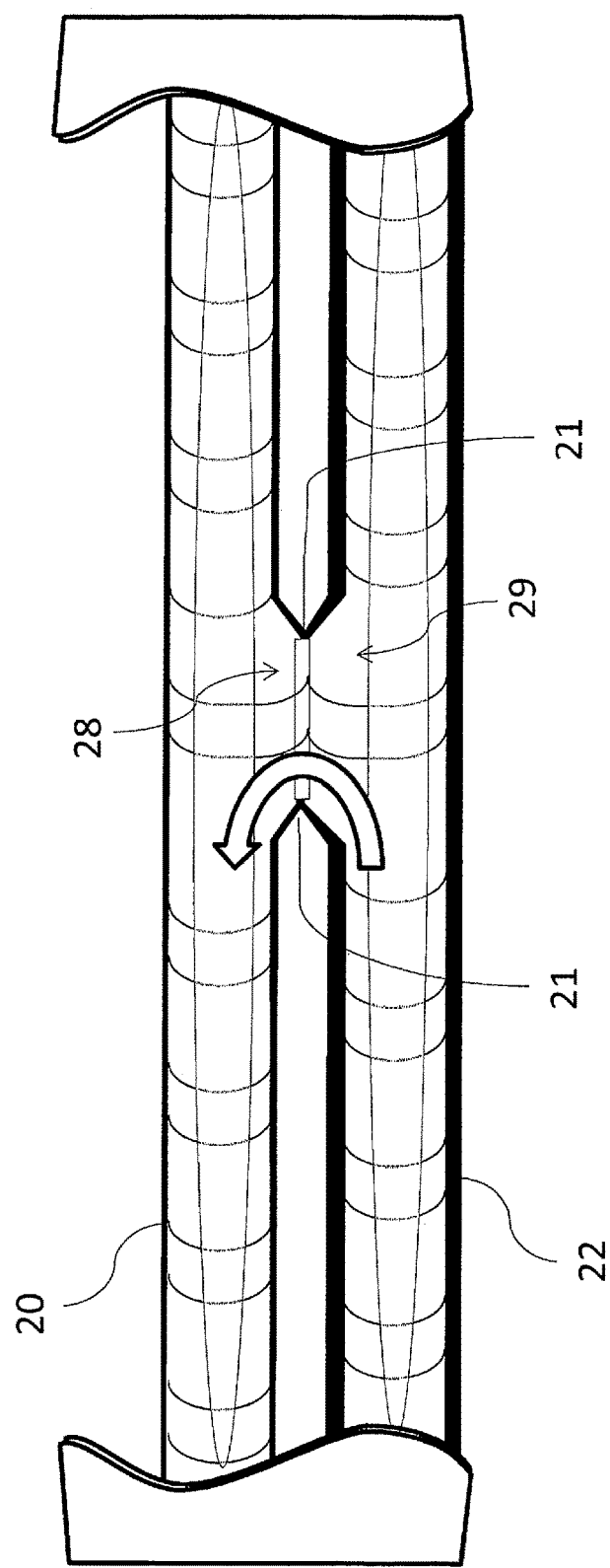
FIG. 11 is a diagram showing the flow through vessels as a result of the device's service.

Now that fistula 25 has been fully formed, as described in block 50 of FIG. 13, the entire instrument 1 and, optionally, guidewire 17 are withdrawn. Fluid flow is now established between vessels 20 and 22 through fistula 25 as shown in FIG. 11.

In another modified embodiment, embedded heater 12 and heating element 8 may be merged into the same component. The welding and cutting surfaces can be smaller so as to approximate the dimensions of the heating element, making this change practical. The dimensions of heating element 8 will determine the resistance across power attachment points 11. This resistance in relation to the resistance of the leads conducting energy to heater element 8 is critical. As the resistance across points 11 lowers and approximates the resistance in the leads, the leads will start to burn a good portion of the power, heating up proximal shaft 6 and requiring more energy to be delivered to accomplish the same weld. Heating element is made longer by its serpentine shape, thus increasing its resistance to minimize this effect. Choosing a heating element material with greater resistance will also help. In another modified embodiment, rib relief 15 may be eliminated, and ribs 9 formed to contact a surface on heat spreader 24. The nature of this contact and the shapes of the surfaces may enhance thermal cutting with mechanical cutting. The mechanical cutting may be accomplished by putting sharp edges on the ribs that interact with heat spreader 24 so as to shear tissue. Heat spreader 24 may also have surfaces or edges that work in concert with features on ribs 9 to mechanically cut tissue. These cutting designs maximize the final contact area between ribs 9 and the heat spread so that sufficient heat transfer is available to the spreader to weld tissues together in the next step.

Welding is possible without resilient member 26 and rib relief 15. Tissue will be trapped in a gap controlled by the height of rib 9. The compliance of tissue within that gap will dictate the pressure under which it is welded. In some designs and applications, this is sufficient.

The distal tip 5 can have a uniform conical tapered outer surface, though it can have a variable tapered, sloped outer surface, wherein the outer surface tapers down to the approximate diameter of a guidewire to provide an atraumatic method for passing through the vessel wall. This is especially desirable if sheath 19 is inadvertently removed before distal tip 5 is placed in second vessel 22 and may be viewed as a safety feature. The choice to use this embodiment may be influenced by practitioner skills and experience, anatomy, or patient health.

Device 1 does not require guidewire 17 for placement within sheath 19 as sheath 19 provides secure placement. Consequently, device 1 need not contain provisions for advancement over the guidewire such as lumen 18. Lumen 18 might still exist and serve as a conduit for the transport of materials used in the creation of the fistula such as drugs, biologic fluids, or an adhesive.

+Energy settings may change to weld tissues at other temperatures. Energy may be modulated based upon the impedance of the tissue or temperature feedback. Different energy application durations, or cyclic pulses may be used to maximize welding while minimizing heat transfer to adjacent tissues. The distal tip 5 is configured to have insulating properties to minimize heat transfer to adjacent tissues and/or fluids. As noted above, the entire surface of the proximal and distal heat elements is configured to have a non-stick coating, such as PTFE, to limit tissue adhesion.

It is advantageous for the proximal and distal heating assemblies 2 and 4 to have a non-stick surface to prevent denatured tissue from bonding to the device. If tissue bonds to the device, the weld between vessels can be damaged or weakened during removal of the device. Multiple different coatings or surface modifications can be applied to the components to create a non-stick surface.

In the embodiment of FIG. 3, it is advantageous that a center shaft 16 also have a non-stick surface to prevent coagulated blood and tissue from bonding to the surface and obstructing the annular gap between the outside diameter of the center shaft 16 and the inside diameter of the proximal heating assembly 2. If blood or tissue bonds to or obstructs this annular gap, this may prevent effective compressive force transmission to the distal heating assembly 4 and compromise tissue weld fusion or tissue cutting.

The compression force of the distal heating assembly 4 influences the weld quality of the tissue. If too much pressure is applied, distal heating assembly 4 may quickly cut through the tissue. A balance of heat and pressure is required to dessicate and denature the protein in the tissue to promote adhesion. In order to best achieve this, resilient member 26 is placed behind heat spreader 24. Resilient member 26 may be pre-compressed in its placement between heat spreader 24 and distal tip 5. This will enable resilient member 26 to best approximate a linear force thus ensuring the proper pressure is applied to tissue during welding. Resilient member 26 is preferably made out of silicone. Common compression springs could also be used coiled or Belleville springs made out of bio-compatible materials.

In one embodiment, the lumen 18 is sized to receive a 0.014 inch guidewire, but may be sized to receive guidewires of various diameters. Larger and smaller guidewires are sometimes preferred. Larger diameter guidewires offer more support to transport devices and resist prolapsing. Smaller guidewires are less likely inadvertently penetrate tissues and can navigate tortuosities easier. Such dynamics are known to those familiar with the art.

In one embodiment, the proximal base 10 is cut at an angle θ of 23 degrees, forming a distal diagonal end surface 10*a*. However, the angle θ can be adjusted depending on the particular anatomy of a procedural site and desired anastomosis length. The inventors have found that the angle θ provides advantageous outcomes within a range of about 15-90 degrees, and more particularly within a range of 15-50 degrees, keeping in mind that approximately 23 degrees is presently a particularly preferred angle within that range. These preferred angles/angle ranges result in an optimized oval configuration for the anastomosis which maximizes the cutting surface while also efficiently utilizing available heating energy to create an effective cut and welding zone.

A variety of DC resistive energy profiles may be used to achieve the desired cutting. For example, a rapidly stepped or ramped increase to achieve and maintain a desired temperature setting of 150° C.-600° C. may be applied to cut through the vessel walls.

Regarding materials, in one preferred embodiment, the outside diameter of the center shaft 16 and inside diameter of the proximal heating assembly 2 have a surface finish of <16 Ra, have an annular gap of 0.0005-0.0002 inches, and are coated using a high temperature Parylene. Other nonstick coatings, such as Poly Tetra Fluoro Ethylene (PTFE), Titanium Nitride (TiN), Chromium Nitride (CrN), Dicronite, silicone, or other similar coatings known to those skilled in the art may be used to prevent tissue adherence.

Materials known to work well for proximal base 10 and shaft 4 include Vespel, Celazol, Teflon, Polyimide, Ultem, and ceramics.

Examples of thermally conductive material suitable for the construction of embedded heater 12, and ribs 9, and heat spreader 24 include aluminum, stainless steel, aluminum nitride, or other metal or ceramic materials known to those skilled in the art.

Now, with reference to FIGS. 14-21, a catheter 1*a* usable in the intraluminal anastomotic device 1 shown and described in FIGS. 1-13 is illustrated. As noted above, a function of the catheter 1*a* is to compress tissue within a tissue space 51 disposed between the distal tip 5 and the proximal base 10, and particularly between the proximal surface 5*a* of the distal tip 5 and the distal surface 10*a* of the proximal base 10. The center shaft 16 connects the distal tip 5 to the proximal base 10, and is typically fixedly attached at its distal end to the distal tip 5, and slidably attached at its proximal end to the proximal base 10, so that the shaft 16 can slide within a center lumen 52 in the proximal base 10 (see FIG. 4*a*), in order to permit the distal tip to move axially relative to the proximal base. Having the base attached fixedly, and the tip slidably connected is also possible.

Figure 15:
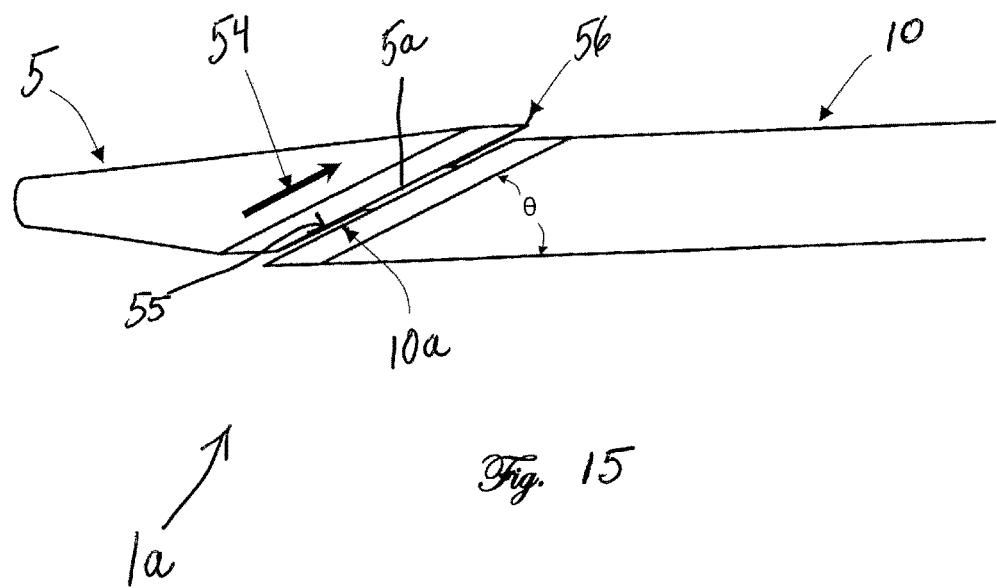
FIG. 15 is a plan view of a catheter like that shown in FIG. 14, illustrating a problem that can occur because of high pressures on the catheter during use.
Figure 16:
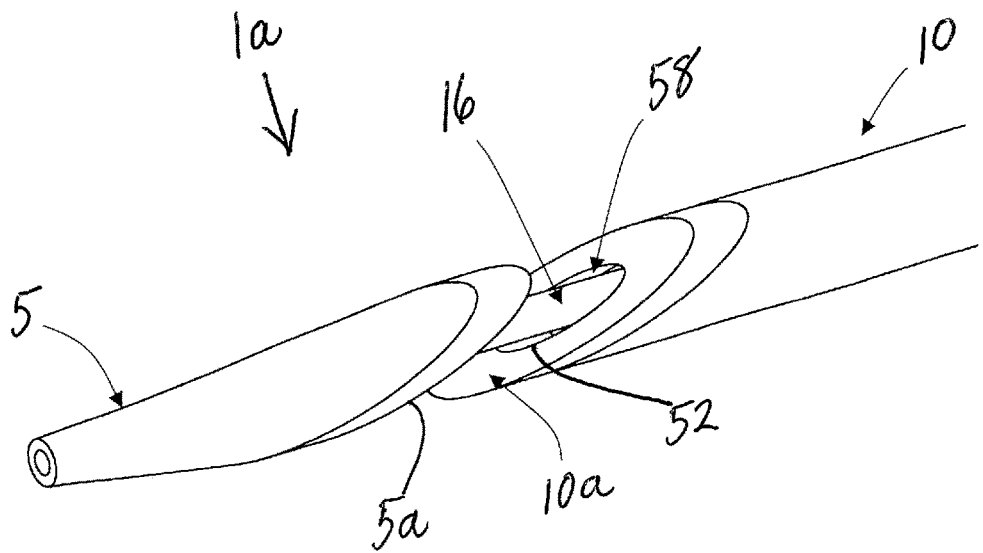
FIG. 16 is an isometric view of the catheter shown in FIGS. 14-15, illustrating one feature that can contribute to or reduce the issue of shifting of the distal tip due to high applied pressures.

The angled catheters of the type shown in the system described in this application absorb significant pressures during use. This pressure is applied as a part of such steps as cutting, welding, or otherwise mechanically manipulating or clamping the tissue. The basic construction of the catheter 1*a* can make it unstable at the pressures it experiences, thereby sometimes causing the distal tip 5 of the catheter to mismatch with the proximal base 10 in the direction of arrow 54 (FIG. 15). As the distal tip 5 exerts pressure on the proximal base 10, the distal tip 5 tends to slide on its angled surface 5*a*, relative to the proximal base angled surface 10*a*. Only the stiffness of the shaft 16 opposes this tendency to slide. But, the pressures can be such that the shaft 16 either bends or distorts its foundation in the proximal base 10, thereby allowing the distal tip 5 to slide down along its angled surface, as shown by the arrow 54. As this sliding continues, a proximal point 56 along a peripheral edge 55 of the distal diagonal surface 10*a* mismatches with its mating base and becomes a barb 56 (FIG. 15) that may snag on tissue or other catheter instruments, thereby impairing function and/or catching on tissue so that removal of the instrument becomes more difficult.

Tension on the center shaft 16 magnifies the side load by the inverse of the sine of angle θ, shown also in FIG. 15. This is three times the tension in the shaft when the angle θ is about 20 degrees. This phenomenon powers the distortion that causes the barb 56.

The center shaft 16 in this design is the stabilizing member in the structure, that keeps the angled faces 5*a* and 10*a* aligned. Keeping a tolerance or gap 58 (FIG. 16) close between the shaft and the lumen 52 is one way to keep the distal tip 5 from side-shifting due to the taper. However, a relatively loose tolerance 58 is shown, because a tight tolerance causes other difficulties in manufacturing and operation. In some uses of the catheter 1*a*, the angled surfaces 5*a* and 10*a*, as described above, are heated. If the materials used in the construction of the catheter are subject to softening by this heat, they may deform when subject to high sideloads caused by applied pressure. This heating, therefore, tends to magnify the problem of the creation of the barb 56.

Figure 17:
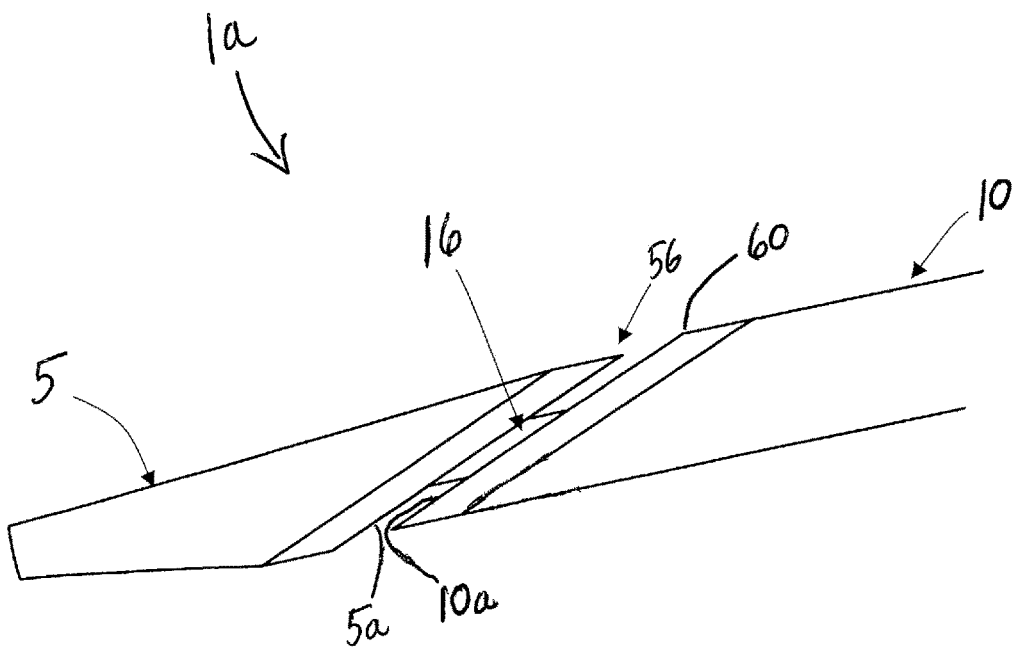
FIG. 17 illustrates a catheter like those shown in FIGS. 14-16 wherein the distal tip has been shifted to counter expected changes in the catheter because of applied pressure during use.

In many circumstances, catheter 1*a* may be used in controllable circumstances. The amount of tension on the center shaft 16 may always be similar, the type of tissue clamped within the tissue space 51 may always be the same, the thickness of the tissue may always be the same, and the environmental temperature may always be the same. If the catheter 1*a* is intended for use in these kinds of predictable environments, the distance through which the distal tip 5 slides along the angled surfaces 5*a*, 10*a* is likely to be predictable. This predictability enables the catheter 1*a* to function without snagging tissue if it is pre-disposed in the opposite direction. This concept is illustrated in FIG. 17, wherein the catheter 1*a* is constructed with the proximal point 56 shifted to be offset in a direction opposite to arrow 54 by a distance equal to the anticipated distance to be traversed during the sliding process noted above. Thus, when the catheter 1*a* is fully loaded, the barb 56 will only slide to a position even with edge 60 on distal surface 10*a*, thereby reducing or eliminating the tendency to snag tissue.

Tensions in the center shaft 16 can easily overcome the same shaft's ability to resist a side load, especially if the angle θ is less than 35 degrees. This will happen even if the tolerances 58 on the center shaft and its bearing hole 52 are very tight. Other mechanical features must be brought into play to enable the rest of the system to function properly.

There are many interactions that such a catheter 1*a* may have with other components, and many ways in which this offset barb 56 can be moderated to a point of functionality. The simplest way is to shorten the length of the barb 56 and to put a full radius 62 on it. Unfortunately, this approach also decreases the catheter's operating footprint with the tissue which may also decrease its functionality.

Figure 19:
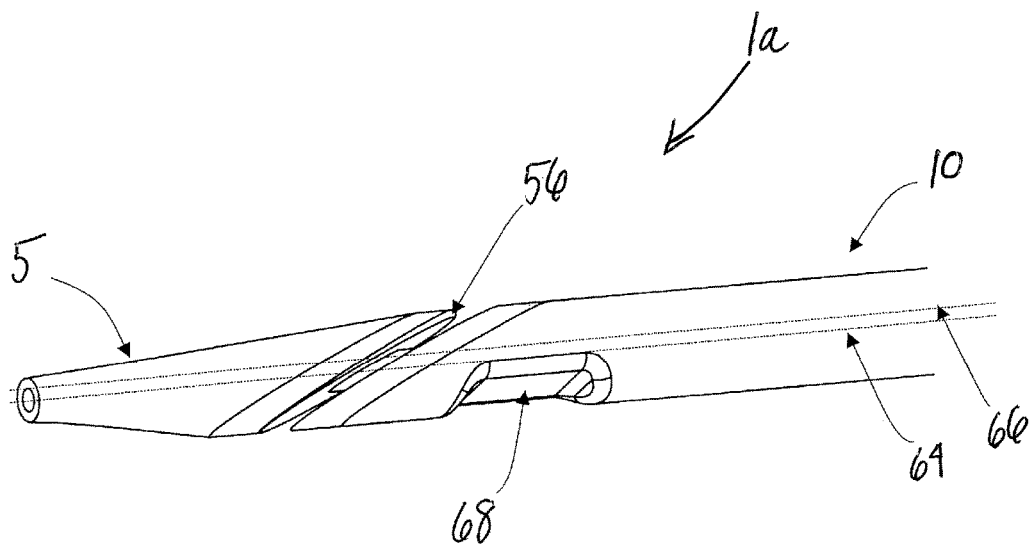
FIG. 19 illustrates a relief feature included on a catheter like those shown in FIGS. 14-18 for improving functionality of the catheter during use.

FIG. 19 shows a modified embodiment of the catheter 1*a* which effectively shifts an original operating axis 64 of the catheter 1*a* upwardly to new axis 66. This axial shift is in the direction of the barb 56. A relief recess 68 facilitates this shift by allowing the catheter to move down its operating aperture. This enables the barb 56 to be free of intimate contact with the top of the catheter's operating aperture, thus preventing the barb 56 from interacting with and snaring tissue or other catheter-related system components, such as a sheath.

In other catheter designs, it may be possible to insert a stop 70 on the angled base so that the barb 56 hits the stop when higher tensional forces cause the catheter tip to mismatch. Such a stop requires shortening the distal tip angle 72 in a manner similar to that shown in FIG. 18.

Figure 18:
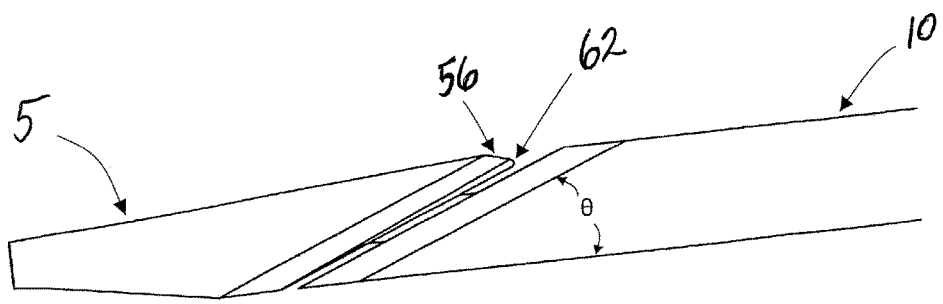
FIG. 18 illustrates a catheter like those shown in FIGS. 14-17 wherein another change has been introduced to reduce issues related to shifting of the distal tip during use.
Figure 20:
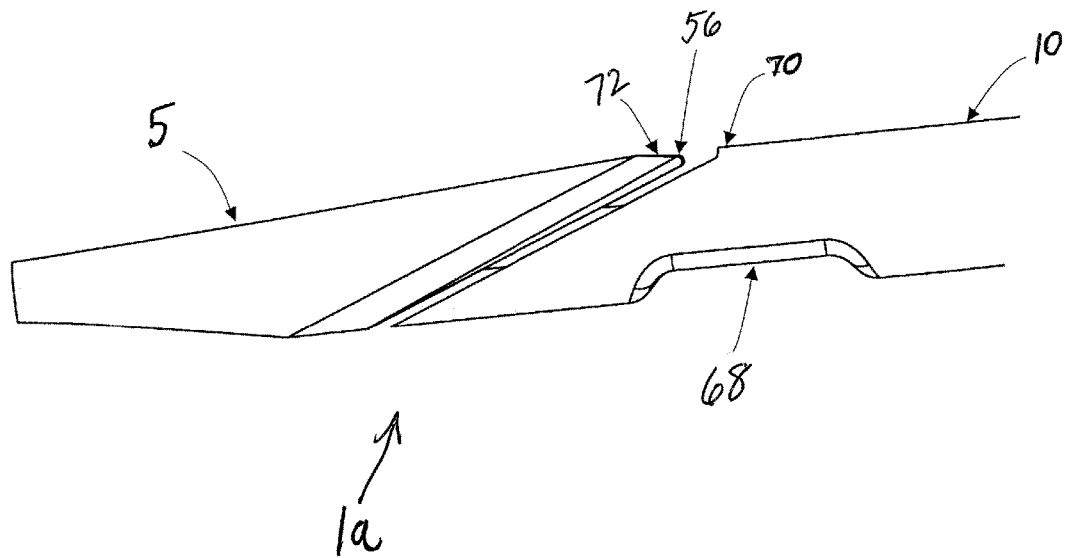
FIG. 20 shows a catheter similar to that shown in FIG. 19, wherein a further feature has been incorporated into the design to improve functionality.
Figure 21:
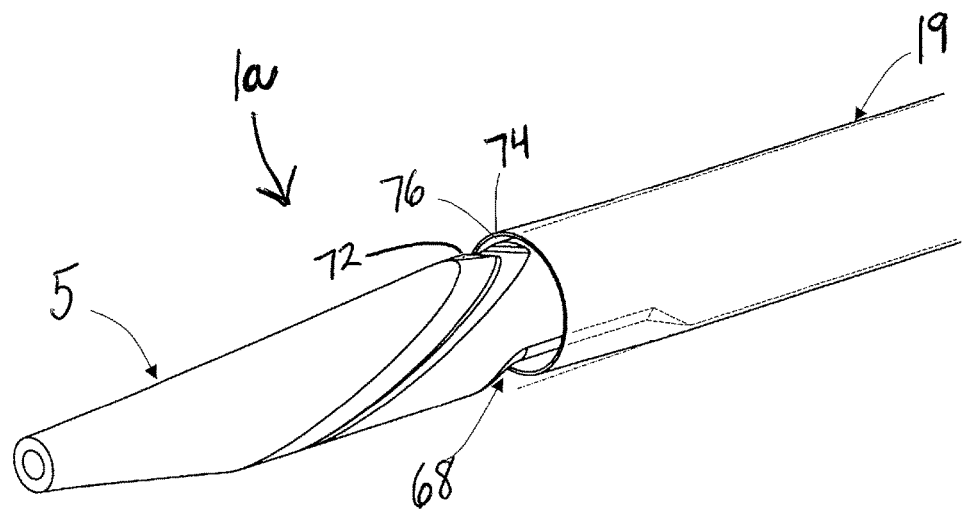
FIG. 21 illustrates a catheter like those shown in FIGS. 19 and 20 disposed within an introducer sheath.

FIG. 21 shows the catheter 1*a* inside of a sheath 19. Introducer sheaths are commonly used in connection with a dilator and guidewire to gain access to blood vessels. The distal tip of the sheath is very thin and fits tightly with the outside of the catheter 1*a*. This is a situation where barb 56 will catch a distal end 74 of the sheath 19 very easily. Because the relief 68 is incorporated into the catheter 1*a*, space 76 is generated due to the gentle shifting of the sheath distal end 74 within the relief 68. Space 76 allows the barb 56 to pass into the sheath distal end 74, as shown in FIG. 21, thereby eliminating the aforementioned snagging risk. In this embodiment, the barb 56 is radiused, as shown in FIGS. 18 and 20.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A catheter system for creating an arteriovenous (AV) fistula, comprising:
    a proximal base having a distal diagonal end surface;
    a distal tip connected to the proximal base and movable relative to the proximal base, the distal tip having a proximal diagonal end surface, the distal diagonal end surface and the proximal diagonal end surface being adapted to contact opposing sides of a tissue portion to create the fistula;
    a peripheral edge defining said proximal diagonal end surface;
    a proximal point on said peripheral edge; and
    a relief recess disposed along a side wall defining a length of the proximal base, wherein the relief recess has a depth extending radially inwardly from an outer surface of the side wall toward a straight operating axis along which an entire length of the proximal base is disposed, the relief recess having an axial length which is greater than the depth of the recess.

2. The catheter system as recited in claim 1, wherein the relief recess is peripherally spaced from the proximal point on an opposed side of the straight operating axis relative to the proximal point.

3. The catheter system as recited in claim 1, and further comprising a sheath adapted to be disposed about said proximal base, the sheath having a distal end wherein a first portion of the sheath distal end is adapted to be disposed in said relief recess when the sheath is disposed about said proximal base, and further wherein a space is created at a second portion of the sheath distal end into which the proximal point may pass when the first portion of the sheath distal end is disposed in said relief recess, the second portion of the sheath distal end being radially opposed to the first portion of the sheath distal end.

4. The catheter system as recited in claim 1, and further comprising a stop formed in a peripheral edge of the distal diagonal end surface of the proximal base, the stop being disposed at a peripheral location directly aligned with the proximal point and radially opposed to the relief recess.

5. The system as recited in claim 1, and further comprising a shaft for connecting the distal tip to the proximal base, the shaft being extendable and retractable to extend and retract said distal tip relative to the proximal base.

6. The system as recited in claim 1, and further comprising a heating assembly comprising an energizable heating element disposed on at least one of the distal diagonal end surface and the proximal diagonal end surface.

7. The system as recited in claim 1, wherein said proximal point comprises a fully radiused edge relative to a remaining portion of said peripheral edge.

8. The system as recited in claim 7, wherein the proximal point further comprises a shortened angle.

9. A catheter system for creating an arteriovenous (AV) fistula, comprising:
    a proximal base having a distal diagonal end surface;
    a distal tip connected to the proximal base and movable relative to the proximal base, the distal tip having a proximal diagonal end surface, the distal diagonal end surface and the proximal diagonal end surface being adapted to contact opposing sides of a tissue portion to create the fistula; and
    a relief recess disposed along a side wall defining a length of the proximal base, wherein the relief recess has a depth extending radially inwardly from an outer surface of the side wall toward a straight operating axis along which an entire length of the proximal base is disposed, the relief recess having an axial length which is parallel to the straight operating axis and is greater than the depth of the recess.

10. The catheter system as recited in claim 9, and further comprising:
    a peripheral edge defining said proximal diagonal end surface; and
    a proximal point on said peripheral edge.

11. The catheter system as recited in claim 10, wherein the relief recess is peripherally spaced from the proximal point on an opposed side of the straight operating axis relative to the proximal point.

12. The catheter system as recited in claim 11, and further comprising a sheath adapted to be disposed about said proximal base, the sheath having a distal end wherein a first portion of the sheath distal end is adapted to be disposed in said relief recess when the sheath is disposed about said proximal base, and further wherein a space is created at a second portion of the sheath distal end into which the proximal point may pass when the first portion of the sheath distal end is disposed in said relief recess, the second portion of the sheath distal end being radially opposed to the first portion of the sheath distal end.

13. The catheter system as recited in claim 11, and further comprising a stop formed in a peripheral edge of the distal diagonal end surface of the proximal base, the stop being disposed at a peripheral location directly aligned with the proximal point and radially opposed to the relief recess.

14. The system as recited in claim 10, wherein said proximal point comprises a fully radiused edge relative to a remaining portion of said peripheral edge.

15. The system as recited in claim 14, wherein the proximal point further comprises a shortened angle.

16. The system as recited in claim 9, and further comprising a shaft for connecting the distal tip to the proximal base, the shaft being extendable and retractable to extend and retract said distal tip relative to the proximal base.

17. The system as recited in claim 9, and further comprising a heating assembly comprising an energizable heating element disposed on at least one of the distal diagonal end surface and the proximal diagonal end surface.

* * * * *